United States Patent [19]

Loosmore et al.

[11] Patent Number: 5,506,139
[45] Date of Patent: Apr. 9, 1996

[54] ANALOG OF HAEMOPHILUS HIN47 WITH REDUCED PROTEASE ACTIVITY

[75] Inventors: Sheena M. Loosmore, Aurora; Yan-Ping Yang, Willowdale; Pele Chong, Richmond Hill; Raymond P. Oomen, Tottenham; Michel H. Klein, Willowdale, all of Canada

[73] Assignee: Connaught Laboratories Limited, Willowdale, Canada

[21] Appl. No.: 278,091

[22] Filed: Jul. 21, 1994

[51] Int. Cl.$^6$ ............ C12N 9/52; C12N 15/31; C12N 15/57
[52] U.S. Cl. ............ 435/252.3; 435/220; 435/320.1; 536/23.2; 536/23.7; 935/10; 935/14
[58] Field of Search ............ 536/23.2, 23.7; 435/220, 320.1, 252.3; 935/10, 14

[56] References Cited

FOREIGN PATENT DOCUMENTS

| WO92/10936 | 7/1992 | WIPO . |
| WO92/11367 | 7/1992 | WIPO . |
| WO94/00149 | 1/1994 | WIPO . |
| WO94/12641 | 6/1994 | WIPO . |

OTHER PUBLICATIONS

Zangwill et al, 1993 MMWR 42:1–15.
Schoendorf et al, 1994 Pediatrics 93:663–8.
Brenner et al, 1988 Nature 334:528–530.
O'Hagan 1992 Clin. Pharmokinet. 22:1–10.
Ulmer et al, 1993 Curr. Opinion. Invest. Drugs 2:983–989.
Chang et al, 1978 Nature 275:617.
Goeddel et al, 1980 Nucl. Acid. Res. 8:4057.
Harkness et al, 1992 J. Bacteriol. 174:2425–2430.
Loeb et al, 1987 Infec. Immun. 55:2612–2618.
Holmes and Quigley 1981. Analyt. Biochem. 114:193–197.
Young and Davis 1985 Gene 38:31–38.
Panezutti et al, 1993 Infec. Immun. 61:1867–72.

Primary Examiner—Robert A. Wax
Assistant Examiner—Keith D. Hendricks
Attorney, Agent, or Firm—Sim & McBurney

[57] ABSTRACT

An isolated and purified analog of *Haemophilus influenzae* Hin47 protein has a decreased protease activity which is less than about 10% of that of natural Hin47 protein and preferably substantially the same immunogenic properties as natural Hin47 protein. An isolated an purified nucleic acid molecule encoding the Hin47 analog may be provided in a recombinant plasmid which may be introduced into a cell which is grown to produce the Hin47 analog. Immunogenic compositions comprising the Hin47 analog and the encoding nucleic acid may be formulated as vaccines for in vivo administration to a host, including a human, to confer protection against diseases caused by a bacterial pathogen, including Haemophilus species, such as *Haemophilus influenzae*, that produces Hin47 protein or a protein capable of inducing antibodies in the host specifically reactive with Hin47 protein. The Hin47 analog and the encoding nucleic acid also may be employed in diagnostic applications.

26 Claims, 23 Drawing Sheets

FIG. 2A.
SB33 Hin47 sequence

```
GGATCCGTTAATACTGAAATAAATGGCACACCTTTTTCACGCATTTGGGCAAGTACAGCA
         10        20        30        40        50        60

CTGGTTTTTGCCATTTGCATTAAAAGAGAATAATGCTTCCCTGCATACGAGCACCACTTC
         70        80        90       100       110       120

GCAGAGAAACATACAAAACGGACAATTCATTTCCATTCGCTTTTTCAGCCGCTTTAACAAAT
        130       140       150       160       170       180

TTTGCACCAACTACAGAACCCATTGAACCGCCCATAAAAGCAAAGTTCGATGCAGCCACA
        190       200       210       220       230       240

ACAATTGGCATATCATAAAGTGTACCTGTCATAGTAATTAGCGCATCTTTTCTCGCCCGTT
        250       260       270       280       290       300

TCTTTTTGTGCCGCATTGATACGATCTTTATATTTCTTTAAATCTTTAAATTTTAAAATA
        310       320       330       340       350       360
```

FIG.2B.

```
TCTTTTGGTTCTAAATCTGCCGCAATTTCTTGGCTTTGAATCTTCGTCCAATAAATTTAAT
370        380        390        400        410        420

AAACGCTCACGAGCATCAATACGCATATGATGACCACATTTCGGGCAAACATACAGATTA
430        440        450        460        470        480

CGTTTGAGTTCTTCACTATAAAGTACTTGTTCACAAGCAGTACATTTTGTCCATACGCCT
490        500        510        520        530        540

TCTGGCACATTGGCTTTTCGAGTGGAAGAAGGACTTTTACTAAAAATTCGGTTAATC
550        560        570        580        590        600

CAGCTCATTTTTTGACCTTTTTATTGACTAGAAAATTGCGCGTATTAGAACATAAATTTA
610        620        630        640        650        660

TAGAATTTGCTACTTGTAAGACCGTTTTTGTACTGCTCCCGATTTCCTTTTAAACAAGATA
670        680        690        700        710        720

ATTTGCTCTCCCTCTTATTGAACATTTTTATTTTTTGTCTTACTGACCACGTTATCT
730        740        750        760        770        780
```

FIG. 2C.

```
                                          met lys thr arg phe val leu asn ser ile ala leu
                                          MET LYS THR ARG PHE VAL LEU ASN SER ILE ALA LEU
GAAATTTATTTTGGAGTATTTATGAAAAAAACACGTTTGTACTAAATAGTATTGCACTT
         790           800           810           820           830           840
                                          atgaaaaaacacgttttgtattaaatagtattgcactt gly leu ser val leu ser thr ser phe val ala gln ala thr leu pro ser phe val ser
GLY LEU SER VAL LEU SER THR SER PHE VAL ALA GLN ALA THR LEU PRO SER PHE VAL SER
GGATTAAGTGTATTAAGCACATCATTTGTTGCTCAAGCCACTTTGCCAAGTTTTGTTTCG
        850           860           870           880           890           900
g g glu gln asn ser leu ala pro met leu glu lys val asp ser arg ser pro phe leu asp asp ile pro glu glu
GLU GLN ASN SER LEU ALA PRO MET LEU GLU LYS VAL ASP SER ARG SER PRO PHE LEU ASP ASP ILE PRO GLU GLU
GAACAAAACAGTCTTGCACCAATGTTAGAAAAAGTAGATTCTCGTTCTCCTTTCCTTGATGATATTCCTGAAGAA
        910           920           930           940           950           960           1010           1020 val glu gly lys ala lys val asp ser arg ser pro phe leu asp asp ile pro glu glu lys
VAL GLU GLY LYS ALA LYS VAL ASP SER ARG SER PRO PHE LEU ASP ASP ILE PRO GLU GLU LYS
GTTGAAGGAAAAGCTAAAGTAGATTCTCGTTCTCCTTTCCTTGATGATATTCCTGAAGAA
        970           980           990           1000          1010          1020 phe lys phe phe gly asp arg phe ala glu gln phe ala glu gln phe ala gly arg gly glu asn gln lys
PHE LYS PHE PHE GLY ASP ARG PHE ALA GLU GLN PHE ALA GLY ARG GLY GLU ASN GLN LYS
TTTAAATTCTTCTTTTGGCGATCGTTTTGCCGAACAATTGGTGGACGTGGAGAATCAAAG
        1030          1040          1050          1060          1070          1080
```

FIG. 2D.

```
ARG ASN PHE ARG GLY LEU GLY SER GLY VAL ILE ILE ASN ALA SER LYS GLY TYR VAL LEU
CGTAACTTCCGTGGTTTAGGTTCTGGTGTGTCATTATTAATGCAAGCAAAGGCTATGTTTTA
    1090              1100              1110              1120              1130              1140

THR ASN ASN HIS VAL ILE ASP GLU ALA ASP LYS ILE THR VAL GLN LEU GLN ASP GLY ARG
ACCAATAATCATGTTATTGATGAAGCTGATAAAATTACCGTGCAATTACAAGATGGGCGT
    1150              1160              1170              1180              1190              1200

GLU PHE LYS ALA LYS LEU VAL GLY LYS ASP GLU LEU SER ASP ILE ALA LEU VAL GLN LEU
GAATTTAAAGCAAAATTAGTGGGTAAAGATGAACTATCAGATATTGCATTAGTACAGCTT
    1210              1220              1230              1240              1250              1260

GLU LYS PRO SER ASN LEU THR GLU ILE LYS PHE ALA ASP LYS LEU ARG VAL GLY
GAAAAACCAAGTAATTTAACAGAAATCAAATTTGCTGATTCCGACAAATTACGCGTAGGC
    1270              1280              1290              1300              1310              1320

ASP PHE THR VAL ALA ILE GLY ASN PRO PHE GLY LEU GLY GLN THR VAL THR SER GLY ILE
GATTTCACTGTTGCAATCGGTAATCCATTTGGTTTAGGTCAAACTGTGACATCAGGTATT
    1330              1340              1350              1360              1370              1380

VAL SER ALA LEU GLY ARG SER GLY ASP SER GLY THR TYR GLU ASN TYR ILE GLN
GTTTCTGCATTGGGTCGTTCAACAGGTTCTGACAGTGGCACTTATGAAAACTATATTCAA
    1390              1400              1410              1420              1430              1440

THR ASP ALA ALA VAL ASN ARG GLY ASN SER GLY GLY ALA LEU VAL ASN LEU ASN GLY GLU
ACCGATGCAGCAGTAAACCGCGGTAATTCGGGTGGAGCGTTAGTAAACTTAAATGGCGAA
    1450              1460              1470              1480              1490              1500
```

FIG.2E.

```
LEU ILE GLY ILE ASN THR ALA ILE ILE SER PRO SER GLY GLY ASN ALA GLY ILE ALA PHE
CTTATTGGAATTAATACCGCAATTATTTCTCCAAGCGGTGGCAATGCAGGAATTGCCTTT
         1510              1520              1530              1540              1550              1560

ALA ILE PRO SER ASN GLN ALA SER ASN LEU VAL GLN ILE GLN ASN LEU VAL GLN ILE GLN ASN LEU GLU PHE GLY GLN VAL
GCGATTCCAAGTAATCAAGCAAGCAATTAGTGCAAATTTAGAATTTGGTCAAGTG
         1570              1580              1590              1600              1610              1620

ARG ARG GLY LEU LEU GLY ILE LYS GLY LEU GLY LEU ASN ALA ASP LEU ALA LYS ALA PHE
CGTCGCGGATTGCTTGGTATTAAAGGTGGCGAACTCAATGCTGATTTAGCCAAAGCCTTT
         1630              1640              1650              1660              1670              1680

ASN VAL SER ALA GLN GLN GLY ALA PHE VAL SER GLU VAL LEU PRO LYS SER ALA ALA GLU
AATGTAAGCGCGCAACAAGGCGCATTTGTAAGTGAAGTTTTACCGAAATCTGCTGCTGAA
         1690              1700              1710              1720              1730              1740

LYS ALA GLY LEU LYS ALA GLY ASP ILE ILE THR ALA MET ASN GLY GLN LYS ILE SER SER
AAAGCAGGACTTAAAGCGGGCGATATTATCACGGCGATGAACGGTCAAAAAATCTCAAGT
         1750              1760              1770              1780              1790              1800

PHE ALA GLU ILE ARG ALA LYS ILE ALA GLY LYS THR THR GLY ALA GLY LYS GLU ILE SER LEU THR
TTCGCTGAAATTCGTGCAAAAATCGCAAACCACTGGTGCAGGCAAAGAGATTAGCTTGACT
         1810              1820              1830              1840              1850              1860
```

FIG. 2F.

```
TYR LEU ARG ASP GLY LYS SER HIS ASP VAL LYS MET LYS LEU GLN ALA ASP ASP SER SER
TACTTACGTGATGGCAAATCCCACGACGTTAAAATGAAATTACAAGCGGATGATAGTAGC
    1870                1880                1890                1900                1910                1920

GLN LEU SER SER LYS THR GLU LEU PRO ALA LEU ASP GLY ALA THR LEU LYS ASP TYR ASP
CAACTTTCCTCAAAAACTGAGTGCCCTGCATTAGATGGTGCAACATTGAAAGACTACGAT
    1930                1940                1950                1960                1970                1980

ALA LYS GLY VAL LYS SER GLY ILE ILE GLN PRO ASN SER LEU ALA ALA GLN
GCTAAAGGCGTTAAAAGGAATTCACAAAATTCAACCTAATTCGCTGGCTGCACAA
    1990                2000                2010                2020                2030                2040

ARG GLY LEU LYS SER GLY ASP ILE ILE GLY ILE LEU ASN ARG GLN MET ILE GLU ASN ILE
CGTGGGTTTAAAATCGGGCGATATTATTGGTATTAATCGTCAAATGATCGAAAACATT
    2050                2060                2070                2080                2090                2100

ARG GLU LEU ASN LYS VAL LEU GLU THR GLU PRO SER ALA VAL ALA LEU ASN ILE LEU ARG
CGTGAATTAAATAAAGTGCTTGAAACTGAACCGTCAGCAGTTGCACTTAATATTTTACGA
    2110                2120                2130                2140                2150                2160

GLY ASP SER ASN PHE TYR LEU LEU VAL GLN ***
GGTGACAGTAATTTCTATTTATTAGTGCAATAATCTGCTTGATATATTTAAGAAAAAAGT
    2170                2180                2190                2200                2210                2220
```

FIG. 2G.

```
CCGATCACAAATGATCGGGCTTCTTTTTATGCAGCAATCGTTCTTAACAAATCCACCACAA
2230                2240                2250                2260                2270                2280

ATTCTAACCGCACTTTGTTATCAGATAAATCTTTCATGAACTTAAATTTTAATGGGCCAT
2290                2300                2310                2320                2330                2340

CAAATCGATACACAATAGGTTCTTTTTGAATTAATTGAATAAATTTATCTGGATTCACTT
2350                2360                2370                2380                2390                2400

GTGCTTTTTGCTGAAAACTCAATAAAACCGCCCTTGTGTTCCTGCATCAATTCGCACAACTT
2410                2420                2430                2440                2450                2460

TCAACGGCTCAACCAACAAACGCAATTCTGCAATTTGCAGTAAATTTTTGTTGCATCAG
2470                2480                2490                2500                2510                2520

GCAATAATCCGAATCGATCTATTAACTCAACTTTTAATTCATCTAATTCTGCTTTACTCT
2530                2540                2550                2560                2570                2580

CTGCTGCAGCAATGCGTTTATAAAAGGATAAACGCATATTCACGTCTCCTAGATAATCAT
2590                2600                2610                2620                2630                2640
```

FIG. 2H.

```
CAGGCAGTAAAGCAGGCACACGCAATTCAATATCCGCTTGTTGTTGCGTCAATTCTTCTA
    2650          2660          2670          2680          2690      2700

ATGATGGTTCACGCCCTTCTTTTAACGCTTTAACCGCTGCATCCAATAATTCCATATAAA
    2710          2720          2730          2740          2750      2760

GCGAAAAACCGATGCTTTCAATTTGTCCACTTTGTTCCAAGTAATTCGCCCGGCAC
    2770          2780          2790          2800          2810      2820

CACGAATCTCTAAATCGTGGGTTGCCAAGATAAAACCAGCCCCAAGATTATCAAGATTTT
    2830          2840          2850          2860          2870      2880

CCAACGCATCTAGA
    2890
```

FIG. 3A.

Comparison of Hin47 with E.coli htrA and S.typhimurium htrA

```
MKKIRFVINSIAIGIS---VLS-TSFVAQATLPSFVSEQ--NSLAPMLEKVQP            Hin47
....TLA.SRL..S..-IA..PL.AT.AE.-S.ATTA.QMP...........M.           E. coli
....--T.AMS..A..LGIA..PL.AT.AE.SS.AMTA.QMP...........M.          S. typh AVVTLSVEGKAKV-DSRSP-----FLDDIP--EEFKFFGDRF--A                    Hin47
S...SIN...STT.NIP.M.RNFQQF.G..S.FCQ.GSP.QSSP.CQG                 E. coli
S...SIN...STT.NIP.M.RNFQQF.G..S.FCQDGSP.QNSP.CQG                 S. typh EQFGGGREGESKRNFRGLGSGVIINASKGYVLINNHVIDEADKITVQLQDGREFK          Hin47
G.G.G.NG.GQQQK.MA.......D.D....V......V.N.TV.K...S....K.D       E. coli
GGN.GN.GQQQK.MA.......D.A.....V......V.N.SV.K...S....K.D        S. typh AKLVGKDELSDIALVQLEKPSNLTEKFADSDKLRVGDFTVAIGNPF                   Hin47
..M.....PR.....I.IQN.K...A.M...A.....Y.G........                E. coli
...V.....PR.....I.IQN.K...A.L...A.....Y.........                S. typh GLQQIVISGIVSALGRSTGDSGTYENYIQIDAAVNRGNSGGALMLNGELIG
..E........-LNAEN...F......I...........
..E........-LNVEN...F......I...........
```

FIG. 3B.

```
                     INTAIISPSGNAGIAFAIPSNQASNLVQQILEFGQVRRGLLGKKG    Hin47
                     ...LA.D...I.G......MVK..TS.MV.Y...K.E...M.T    E. coli
                     ...LA.D...I.G......MVK..TS.MV.Y......E...M.T   S. typh EINADLAKAFNVSAQQGAFVSEVLPKSAAEKAGLKAGDIITAMNQKISSFAE
...SE.....MK.D..R.....Q...N.S.A...I....V..SL..KP......A
...SE.....MK.D..R.....Q.M.N.S.A...I....V..SL..KP......A IRAKIATIGAGKEISLTYLRDGKSHDVKMKLQADDSSQLSSKIELPA   Hin47
                     L..QVG.MPV.SKIT.GL.....QVN.NLE..QSSQN.VD.SSIFNG  E. coli
                     L..QVG.MPV.SK....GL..E..AIT.NLE..QSSQ..VD.S.IFSG S. typh LDGA---TLKDYDAKGVKGIEITKIQPNSLAAQRGLKSGDIIIGINRQMIENIR
IE...EMSN.GK.QGV.VNNVK.-----GIP...I....K.V...A.Q.AVK..A
IE...EMSN.GQ.KGV.VSSVKA------..P...I....K.V...A.Q.PVK..A EINKVLETEPSAVAINIILRGDSNFYLLVQ*    Hin47
                     ..R...DSK..VL.....Q....--RH.P.N*   E. coli
                     ..R.I.DSK..VL.....Q.....SI....M.*  S. typh
```

FIG. 4A.

```
TON   :                    IVGGYKCEKNSQPMQVAVIN------E----YLCGG VLID
PKAAB:                    IIGGRECEKNSHPMQVAIYHY----SS----FQCGG VLVN
PIN   :                    IVGGYTCGANIVPYQVSLN------SGY---HFCGG SLIN
CHAA  :                    IVNGEEAVPGSWPWQVSLQDK----TGF---HFCGG SLIN
EST   :                    VVGGTEAQRNSWPSQISLQYRSGSSWA----HICGG TLIR
RP2A  :                    IIGGVESIPHSRPYMAHLDIV----TEKGLRVICGG FLIS
SGT   :                    VVGGTRAAQGEFPFMVRLSM-----------GCGG ALYA
SGBE  :                ISGG--------DAIYSS-------------TGRCSLGFNVRSGS
SGA   :                 IAGG--------EAITIG-------------GSRCSLGFNVSVNG
ALP   :                ANIVGG-------IEYSIN-------------NASLCSVGFSVTRGA
hin47:                AEQFGG         RGESKR             N FRGLGSGVIINAS
                      ******                            **
con                   <------>                      <------->

# (His57)
TON   : ------PSWVITAAHCY----S------N-NYQ-VLLGRNNLFK-DEPFAQRRLV
PKAAB: ------PKWVLTAAHCK----N------DNYEV-WL-GRHNLFENENT-AQFFGV
PIN   : ------SQWVSAAHCY----X------SGIQV-RL-GEDNINVEGN-EQFISA
CHAA  : ------ENWVVTAAHCG----V------TISDV-VVAGEFDQGSSSEK-IQKLKI
EST   : ------QNWMIAAHCV----D------RELIFRVVGEHNLNQNGT-EQYVGV
RP2A  : ------RQFVLTAAHCK------------GREIT-VILGAHDVRKREST-QQKIKV
SGT   : ------QDIVLTAAHCV---SGSGNNTSIT-ATGVVDL-QSG-A-AVKVRS
```

FIG.4B.

```
SGBE   :                    TYYFLTAGHCT--D-------GATT-VWA--------NS-ARITVL
SGA    :                    VAHALTAGHCT----------NISASW------------SI
ALP    :                    TKGFVTAGHCGIVN-------AT-AR-IG----------GAVVG
Sal.T:                      KGVVVINNHVDNASVIKVQLSDGR
hin47:                      KGYVLINNHVIDEA       DK-TT-VQ---------LQDGRE
                            ********
ccn         X-----<------------->------------->
                                                <---------->
                                                           <---

# (Asp102)
TON    : RQS-FRHPDYIPLI PVHDH---SNDIMLIHLSEPADITGGVKV-------------
PKAAB:   TAD-FPHPGFNLSAD-GKDY---SHDIMLIRLQSPAKITDAVKV-------------
PIN    : SKS--IVHPSYN----------SNIL---NNDIMLIKKSAASLNSRVAS--------
CHAA   : AKV-FKNSKYN-----------SLTI---NNDITLKLSTAASFSQTVSA--------
EST    : QKI-VVHPYWN-----------TDDVAAGYDIATRLAQSVTLNSYQL----------
RP2A   : EKQ-IIHESYN-----------SVPN---LHDIMLIKEKVELTPAVNV----------
SGT    : TKV-LQAPGYN-----G-T----GKDWALIKLAQPIN----QPT-------------
SGBE   : GIT-SGS-SF------------PNNDYGIVRYINITLPX   DGIVG---------
SGA    : GIR-TGT-SF------------PNNDYGITRHSNPAAA    DGRVYLYNGS-----
ALP    : -TFAARV--F------------PGNDRAWSLTSAQTL-----LPRVANGSS------
hin47:   FKAKLVG        KDEL  SDIALVQLEKPSNL      TEIKFADSKLRVGDF
                              **********
ccn        X----<----------->----X------<------>
                                               <---
```

FIG. 4C.

```
TON    : ----IDLPT--KEPKVGSTCLASGWGSTNPS-E-MVVSHDLQCVNIHLLSN
PKAAB  : ----LELPT-QEPE-LGSTCEASGWGSTERGPDFEFPDELQCVQLTLQN
PIN    : ----ISLPT-SCAS-AGIQCLISGWGNTKSS--GISYPDVLKCLKAPILSD
CHAA   : ----VCLPSASDFAAGTTCVTIGWGLIRY---|--ANTPDRLQQASLPLLSN
EST    : ----GVLPRAGTILANNSPCYITGWGLIR-T---NGQLAQTLQQAYLPTVDY
RP2A   : ----VPLPSPSDFTHPGAMCWAAGWGKIGVR---DPT-SYTLREVELRIMDE
SGT    : ----LKIAT--TTAYNQGIFTVAGWGANRE---GGSQQRYLLKANVPFVSD
SGBE   : GQDITSAA   NATVGMAVIRRGSTT----------GIHSGSVTAL
SGA    : YQDITTAG   NAFVGQAVQRSGSTT----------GLRSGSVIGL
ALP    : FVIVRGST---EAAVGAAVCRSGRTT----------GYQGTITAK
hin47  : TVAIGNPFGLGQIVTSGIVSALGRSTI                GSDSGTYENY
                          *********                    ****
con    : ------>          <-------->                   <------>

# (Ser195)
TON    : EKCIE---TYKDNVT-DMLCA-G-E---MEGGK-DTCA---GDSGGPLIC--
PKAAB  : TFCAD---AHPDKVT-ESMLCAGY-L---P---GGKDICM---GDSGGPLIC--
PIN    : SSCKS---AYPGQIT-SNMFCAGY-L---E---GGKDSCQ---GDSGGPVVC--
CHAA   : TNCKK---YMGIKIK-DAMICA-G-A---S---GV-SSOM---GDSGGPLVC--
EST    : AICSSSSMGSTVK-NSMVCA-G-G---D---GVRSGCQ---GDSGGPLHC--
RP2A   : KACVDYRYEYKF----QVCV-GSP---T---TLRAAFM---GDSGGPLIC--
SGT    : AACRS---AYGNELVANEEICA-G-YPDIG--GV-DICQ---GDSGGMFR--
SGBE   : NATVN--YGGGDVV-YGMIRT-N-----------------VCAEPGDSGGPLYS--
```

FIG. 4D.

```
SGA    : NATVN--YGSSGIV-YGMIQT-N-----------VCAQPGDSGSLFA-
ALP    : NVTAN--Y-AEGAV-RGLTQG-N-A---------CMGR--GDSGGSWITS
hin47  :               IQT D A   ****  ********  AVNR GNSGGALVNLN
         *** * *
con           <------->          <-><------->

TON    : D--------GVLQGITSGGA-TP------C-A-KP--K-T-PAIYAKLIKFT-SW
PKAAB  : NG-------MWQGITSMGH-TP------C-GSA---N-K-PSIYIKLIFYL-DW
PIN    : SGK------LQGIVSMGS--G-------C-AQK---N-K-PGVYIKVCNYV-SW
CHAA   : KKN-GAWTLVGIVSMGS-ST--------C-S-T---S-T-PGVYARVTALV-NW
EST    : LVN-GQYAVHGVISFVSRLG--------C-NVT---R-K-PIVFIRVSAYI-SW
RP2A   : ---A-GV---AHGIVSYG----------HPD----A-KPPAIFIRVSTYV-PW
SGT    : KDNADEWIQVGIVSMGY--G--------C-A-R---PGY-PGVYTEVSIFA-SA
SGBE   : G--------TRAIGLTSGGS-GN-----C-S-S---G-G-TIFFQPVTEALVAY
SGA    : G--------STAIGLTSGGS-GN-----C-R-T---G-G-TIFYQPVTEALSAY
ALP    : A--------GQAQGMSGGN-VQSNGNOG-IPASQ-R-SSLFERLQPIL-SQ
hin47  :            GELIGINTAII SP SGGNAG IAFAI P SNQASNLVQQIL
                   ????

con    >                     <------->               <------->
```

FIG.4E.

```
TON   : IKKVMKENP
PKAAB : IDDITENP
PIN   : IKQTIASN
CHAA  : VQQTLAAN
EST   : INNVIASN
RP2A  : INAVIN
SGT   : IASAARIL
SGBE  : GVSVY
SGA   : GATVL
ALP   : YGLSLVIG
hin47 : EFGQVRGLIGIKG
con                    ———→
```

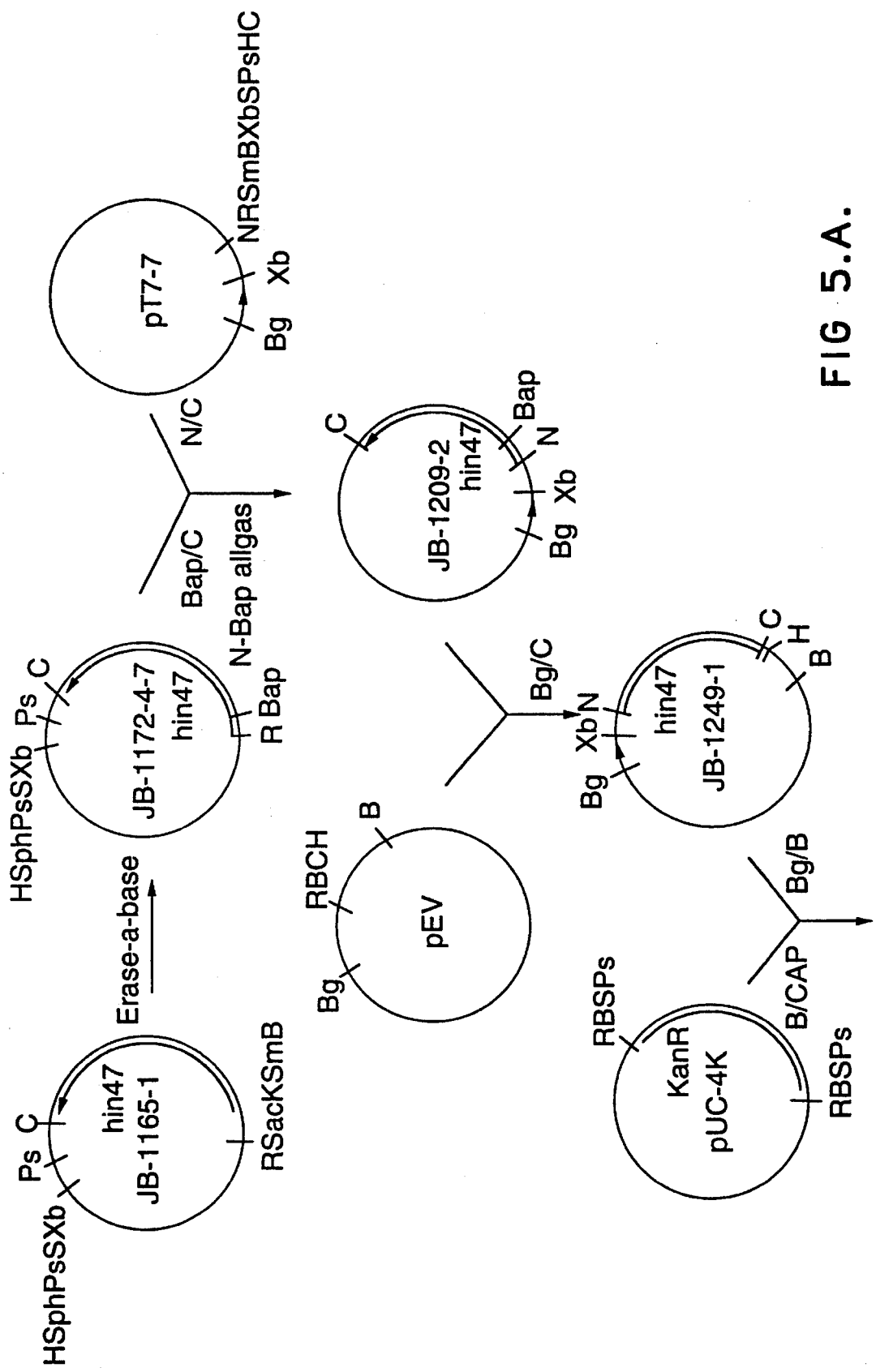
FIG 5.A.

PURIFICATION OF HIN47 MUTANT

Digestion of β-Casein by Hin47

1. β-Casein + Hin47
2. β-Casein + Mutant
3. β-Casein

A. Each lane contains 5μg of β-casein, +/- 20 ng of Hin47 or mutant

B. Each lane contains 5μg of β-casein, +/-0.1 μg of Hin47 or mutant

C. Immuno-blot with rabbit anti-Hin47 antibody

IMMUNO-BLOT ANALYSIS ON THE STABILITIES OF HIN47 AND MUTANT

Day 0    Day 10    Day 20

H: Hin47        1. -20°C

M: Mutant       2. 4°C

Stability Studies on Mixed Antigens
in the Presence of Hin47 or Hin47 Mutant 1. rTBP1
2. rTBP1 + Hin47
3. rTBP1 + Hin47 mutant
4. Hin47
5. Hin47 mutant Comparative Immunogenicity of Hin47 and Mutant in Mice
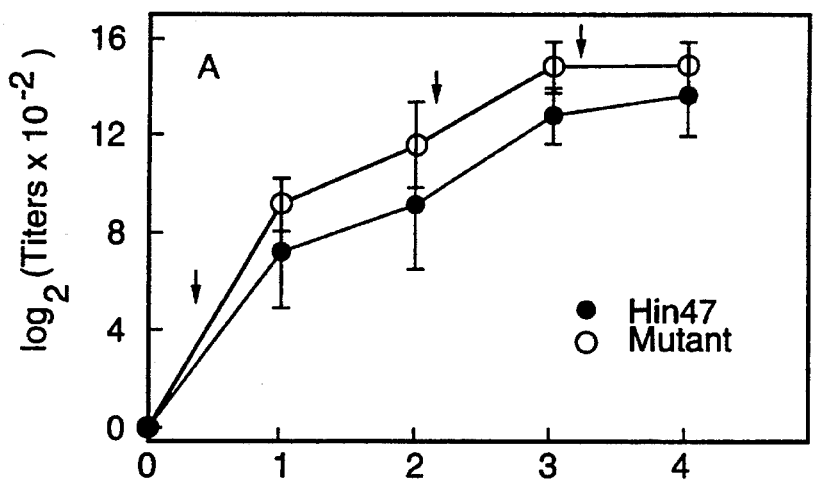
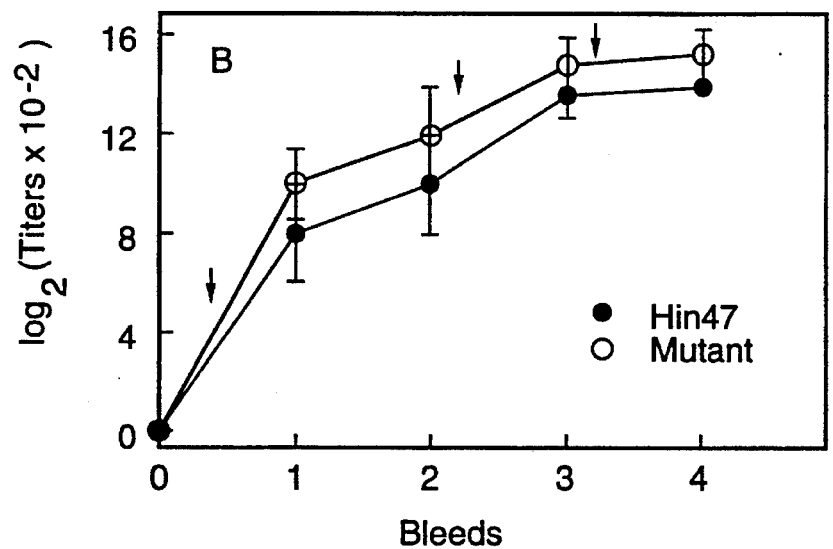
(A) Plat coating: Hin47    (B) Plate coating: mutant
FIG.10.

5,506,139

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
( A ) LENGTH: 2894 base pairs
( B ) TYPE: nucleic acid
( C ) STRANDEDNESS: single
( D ) TOPOLOGY: linear ( x i ) SEQUENCE DESCRIPTION: SEQ ID NO:1:

| | | | | | | |
|---|---|---|---|---|---|---|
| GGATCCGTTA | ATACTGAAAT | AAATGGCACA | CCTTTTTCAC | GCATTTGGGC | AAGTACAGCA | 60 |
| CTGGTTTTTG | CCATTTGCAT | TAAAGAGAAT | AATGCTTCCT | GCATACGAGC | ACCACCACTC | 120 |
| GCAGAGAAAC | ATACAAACGG | ACAATTCATT | TCCATCGCTT | TTTCAGCCGC | TTTAACAAAT | 180 |
| TTTGCACCAA | CTACAGAACC | CATTGAACCG | CCCATAAAAG | CAAAGTTCGA | TGCAGCCACA | 240 |
| ACAATTGGCA | TATCATAAAG | TGTACCTGTC | ATAGTAATTA | GCGCATCTTT | CTCGCCCGTT | 300 |
| TCTTTTTGTG | CCGCATTGAT | ACGATCTTTA | TATTTCTTTA | AATCTTTAAA | TTTTAAAATA | 360 |
| TCTTTTGGTT | CTAAATCTGC | CGCAATTTCT | TGGCTTGAAT | CTTCGTCCAA | TAAATTTAAT | 420 |
| AAACGCTCAC | GAGCATCAAT | ACGCATATGA | TGACCACATT | TCGGGCAAAC | ATACAGATTA | 480 |
| CGTTTGAGTT | CTTCACTATA | AAGTACTTGT | TCACAAGCAG | TACATTTGT | CCATACGCCT | 540 |
| TCTGGCACAT | TGGCTTTTCG | AGTGGAAGAA | GAAGGACTTT | TACTAAAAAT | TCGGTTAATC | 600 |
| CAGCTCATTT | TTTGACCTTT | TTATTGACTA | GAAAATTGCG | CGTATTAGAA | CATAAATTTA | 660 |
| TAGAATTTGC | TACTTGTAAG | ACCGTTTTTG | TACTGCTCCG | ATTTCCTTTT | AAACAAGATA | 720 |
| ATTTGCTCTC | CTCTTATTGA | ACATTTTTTT | TATTTTTTTG | TCTTACTGAC | CACGTTATCT | 780 |
| GAAATTTATT | TTGGAGTATT | TATGAAAAAA | ACACGTTTTG | TACTAAATAG | TATTGCACTT | 840 |
| GGATTAAGTG | TATTAAGCAC | ATCATTTGTT | GCTCAAGCCA | CTTTGCCAAG | TTTTGTTTCG | 900 |
| GAACAAAACA | GTCTTGCACC | AATGTTAGAA | AAAGTACAAC | CTGCCGTTGT | CACTCTTTCC | 960 |
| GTTGAAGGAA | AAGCTAAAGT | AGATTCTCGT | TCTCCTTTCC | TAGACGATAT | TCCTGAAGAA | 1020 |
| TTTAAATTCT | TCTTTGGCGA | TCGTTTTGCC | GAACAATTTG | GTGGACGTGG | AGAATCAAAG | 1080 |
| CGTAACTTCC | GTGGTTTAGG | TTCTGGTGTC | ATTATTAATG | CAAGCAAAGG | CTATGTTTTA | 1140 |
| ACCAATAATC | ATGTTATTGA | TGAAGCTGAT | AAAATTACCG | TGCAATTACA | AGATGGGCGT | 1200 |
| GAATTTAAAG | CAAAATTAGT | GGGTAAAGAT | GAACTATCAG | ATATTGCATT | AGTACAGCTT | 1260 |
| GAAAAACCAA | GTAATTTAAC | AGAAATCAAA | TTTGCTGATT | CCGACAAATT | ACGCGTAGGC | 1320 |
| GATTTCACTG | TTGCAATCGG | TAATCCATTT | GGTTTAGGTC | AAACTGTGAC | ATCAGGTATT | 1380 |
| GTTTCTGCAT | TGGGTCGTTC | AACAGGTTCT | GACAGTGGCA | CTTATGAAAA | CTATATTCAA | 1440 |
| ACCGATGCAG | CAGTAAACCG | CGGTAATTCG | GGTGGAGCGT | TAGTAAACTT | AAATGGCGAA | 1500 |
| CTTATTGGAA | TTAATACCGC | AATTATTTCT | CCAAGCGGTG | GCAATGCAGG | AATTGCCTTT | 1560 |
| GCGATTCCAA | GTAATCAAGC | AAGCAATTTA | GTGCAACAAA | TTTTAGAATT | TGGTCAAGTG | 1620 |
| CGTCGCGGAT | TGCTTGGTAT | TAAAGGTGGC | GAACTCAATG | CTGATTTAGC | CAAAGCCTTT | 1680 |
| AATGTAAGCG | CGCAACAAGG | CGCATTTGTA | AGTGAAGTTT | TACCGAAATC | TGCTGCTGAA | 1740 |
| AAAGCAGGAC | TTAAAGCGGG | CGATATTATC | ACGGCGATGA | ACGGTCAAAA | AATCTCAAGT | 1800 |
| TTCGCTGAAA | TTCGTGCAAA | AATCGCAACC | ACTGGTGCAG | GCAAAGAGAT | TAGCTTGACT | 1860 |

-continued

```
TACTTACGTG ATGGCAAATC CCACGACGTT AAAATGAAAT TACAAGCGGA TGATAGTAGC    1920

CAACTTTCCT CAAAAACTGA GTTGCCTGCA TTAGATGGTG CAACATTGAA AGACTACGAT    1980

GCTAAAGGCG TTAAAGGAAT TGAAATCACA AAAATTCAAC CTAATTCGCT GGCTGCACAA    2040

CGTGGTTTAA AATCGGGCGA TATTATTATT GGTATTAATC GTCAAATGAT CGAAAACATT    2100

CGTGAATTAA ATAAAGTGCT TGAAACTGAA CCGTCAGCAG TTGCACTTAA TATTTTACGA    2160

GGTGACAGTA ATTTCTATTT ATTAGTGCAA TAATCTGCTT GATATATTTA AGAAAAAAGT    2220

CCGATCACAA TGATCGGGCT TCTTTTTATG CAGCAATCGT TCTTAACAAA TCCACCACAA    2280

ATTCTAACCG CACTTTGTTA TCAGATAAAT CTTTCATGAA CTTAAATTTT AATGGGCCAT    2340

CAAATCGATA CACAATAGGT TCTTTTTGAA TTAATTGAAT AAATTTATCT GGATTCACTT    2400

GTGCTTTTGC TGAAAACTCA ATAAACCGC CTTGTGTTCC TGCATCAATT CGCACAACTT    2460

TCAACGGCTC AACCAACAAA CGCAATTCTG CAATTTGCAG TAAATTTTTT GTTGCATCAG    2520

GCAATAATCC GAATCGATCT ATTAACTCAA CTTTTAATTC ATCTAATTCT GCTTTACTCT    2580

CTGCTGCAGC AATGCGTTTA TAAAAGGATA AACGCATATT CACGTCTCCT AGATAATCAT    2640

CAGGCAGTAA AGCAGGCACA CGCAATTCAA TATCCGCTTG TTGTTGCGTC AATTCTTCTA    2700

ATGATGGTTC ACGCCCTTCT TTTAACGCTT TAACCGCTGC ATCCAATAAT TCCATATAAA    2760

GCGAAAAACC GATGCTTTCA ATTTGTCCAC TTTGTTCGTT TCCAAGTAAT TCGCCGGCAC    2820

CACGAATCTC TAAATCGTGG GTTGCCAAGA TAAAACCAGC CCCAAGATTA TCAAGATTTT    2880

CCAAGGCATC TAGA                                                      2894
```

( 2 ) INFORMATION FOR SEQ ID NO:2:

( i ) SEQUENCE CHARACTERISTICS:
        ( A ) LENGTH: 463 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

```
Met Lys Lys Thr Arg Phe Val Leu Asn Ser Ile Ala Leu Gly Leu Ser
 1               5                  10                  15

Val Leu Ser Thr Ser Phe Val Ala Gln Ala Thr Leu Pro Ser Phe Val
             20                  25                  30

Ser Glu Gln Asn Ser Leu Ala Pro Met Leu Glu Lys Val Gln Pro Ala
         35                  40                  45

Val Val Thr Leu Ser Val Glu Gly Lys Ala Lys Val Asp Ser Arg Ser
     50                  55                  60

Pro Phe Leu Asp Asp Ile Pro Glu Glu Phe Lys Phe Phe Gly Asp
65                  70                  75                  80

Arg Phe Ala Glu Gln Phe Gly Gly Arg Gly Glu Ser Lys Arg Asn Phe
                 85                  90                  95

Arg Gly Leu Gly Ser Gly Val Ile Ile Asn Ala Ser Lys Gly Tyr Val
            100                 105                 110

Leu Thr Asn Asn His Val Ile Asp Glu Ala Asp Lys Ile Thr Val Gln
        115                 120                 125

Leu Gln Asp Gly Arg Glu Phe Lys Ala Lys Leu Val Gly Lys Asp Glu
    130                 135                 140

Leu Ser Asp Ile Ala Leu Val Gln Leu Glu Lys Pro Ser Asn Leu Thr
145                 150                 155                 160

Glu Ile Lys Phe Ala Asp Ser Asp Lys Leu Arg Val Gly Asp Phe Thr
                165                 170                 175
```

| | | | | | | | | | | | | | | |
|---|---|---|---|---|---|---|---|---|---|---|---|---|---|---|
| Val | Ala | Ile | Gly | Asn | Pro | Phe | Gly | Leu | Gly | Gln | Thr | Val | Thr | Ser | Gly |
| | | | 180 | | | | | 185 | | | | | 190 | | |
| Ile | Val | Ser | Ala | Leu | Gly | Arg | Ser | Thr | Gly | Ser | Asp | Ser | Gly | Thr | Tyr |
| | | 195 | | | | | 200 | | | | | 205 | | | |
| Glu | Asn | Tyr | Ile | Gln | Thr | Asp | Ala | Ala | Val | Asn | Arg | Gly | Asn | Ser | Gly |
| | 210 | | | | | 215 | | | | | 220 | | | | |
| Gly | Ala | Leu | Val | Asn | Leu | Asn | Gly | Glu | Leu | Ile | Gly | Ile | Asn | Thr | Ala |
| 225 | | | | | 230 | | | | | 235 | | | | | 240 |
| Ile | Ile | Ser | Pro | Ser | Gly | Gly | Asn | Ala | Gly | Ile | Ala | Phe | Ala | Ile | Pro |
| | | | | 245 | | | | | 250 | | | | | 255 | |
| Ser | Asn | Gln | Ala | Ser | Asn | Leu | Val | Gln | Gln | Ile | Leu | Glu | Phe | Gly | Gln |
| | | | 260 | | | | | 265 | | | | | 270 | | |
| Val | Arg | Arg | Gly | Leu | Leu | Gly | Ile | Lys | Gly | Gly | Glu | Leu | Asn | Ala | Asp |
| | | 275 | | | | | 280 | | | | | 285 | | | |
| Leu | Ala | Lys | Ala | Phe | Asn | Val | Ser | Ala | Gln | Gln | Gly | Ala | Phe | Val | Ser |
| | 290 | | | | | 295 | | | | | 300 | | | | |
| Glu | Val | Leu | Pro | Lys | Ser | Ala | Ala | Glu | Lys | Ala | Gly | Leu | Lys | Ala | Gly |
| 305 | | | | | 310 | | | | | 315 | | | | | 320 |
| Asp | Ile | Ile | Thr | Ala | Met | Asn | Gly | Gln | Lys | Ile | Ser | Ser | Phe | Ala | Glu |
| | | | | 325 | | | | | 330 | | | | | 335 | |
| Ile | Arg | Ala | Lys | Ile | Ala | Thr | Thr | Gly | Ala | Gly | Lys | Glu | Ile | Ser | Leu |
| | | | 340 | | | | | 345 | | | | | 350 | | |
| Thr | Tyr | Leu | Arg | Asp | Gly | Lys | Ser | His | Asp | Val | Lys | Met | Lys | Leu | Gln |
| | | 355 | | | | | 360 | | | | | 365 | | | |
| Ala | Asp | Asp | Ser | Ser | Gln | Leu | Ser | Ser | Lys | Thr | Glu | Leu | Pro | Ala | Leu |
| | 370 | | | | | 375 | | | | | 380 | | | | |
| Asp | Gly | Ala | Thr | Leu | Lys | Asp | Tyr | Asp | Ala | Lys | Gly | Val | Lys | Gly | Ile |
| 385 | | | | | 390 | | | | | 395 | | | | | 400 |
| Glu | Ile | Thr | Lys | Ile | Gln | Pro | Asn | Ser | Leu | Ala | Ala | Gln | Arg | Gly | Leu |
| | | | | 405 | | | | | 410 | | | | | 415 | |
| Lys | Ser | Gly | Asp | Ile | Ile | Ile | Gly | Ile | Asn | Arg | Gln | Met | Ile | Glu | Asn |
| | | | 420 | | | | | 425 | | | | | 430 | | |
| Ile | Arg | Glu | Leu | Asn | Lys | Val | Leu | Glu | Thr | Glu | Pro | Ser | Ala | Val | Ala |
| | | 435 | | | | | 440 | | | | | 445 | | | |
| Leu | Asn | Ile | Leu | Arg | Gly | Asp | Ser | Asn | Phe | Tyr | Leu | Leu | Val | Gln |
| | 450 | | | | | 455 | | | | | 460 | | | |

( 2 ) INFORMATION FOR SEQ ID NO:3:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
ATGAAAAAAA CACGTTTTGT ATTAAATAGT ATTGCACTTG G                         41
```

( 2 ) INFORMATION FOR SEQ ID NO:4:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Lys | Lys | Thr | Arg | Phe | Val | Leu | Asn | Ser | Ile | Ala | Leu | Gly | Leu | Ser |
| 1 | | | | 5 | | | | | 10 | | | | | 15 | |

```
Val  Leu  Ser  Thr  Ser  Phe  Val  Ala  Gln  Ala  Thr  Leu  Pro  Ser  Phe  Val
               20                       25                      30

Ser  Glu  Gln  Asn  Ser
               35
```

( 2 ) INFORMATION FOR SEQ ID NO:5:

( i ) SEQUENCE CHARACTERISTICS:
       ( A ) LENGTH: 472 amino acids
       ( B ) TYPE: amino acid
       ( C ) STRANDEDNESS: single
       ( D ) TOPOLOGY: linear ( x i ) SEQUENCE DESCRIPTION: SEQ ID NO:5:

```
Met  Lys  Lys  Thr  Thr  Leu  Ala  Leu  Ser  Arg  Leu  Ala  Leu  Ser  Leu  Ser
1                    5                       10                      15

Leu  Ala  Leu  Ser  Pro  Leu  Ser  Ala  Thr  Ala  Ala  Glu  Thr  Ser  Ser  Ala
               20                       25                      30

Thr  Thr  Ala  Gln  Gln  Met  Pro  Ser  Leu  Ala  Pro  Met  Leu  Glu  Lys  Val
               35                       40                      45

Met  Pro  Ser  Val  Val  Ser  Ile  Asn  Val  Glu  Gly  Ser  Thr  Thr  Val  Asn
     50                            55                      60

Thr  Pro  Arg  Met  Pro  Arg  Asn  Phe  Gln  Gln  Phe  Phe  Gly  Asp  Asp  Ser
65                        70                       75                      80

Pro  Phe  Cys  Gln  Glu  Gly  Ser  Pro  Phe  Gln  Ser  Ser  Pro  Phe  Cys  Gln
                    85                       90                      95

Gly  Gly  Gln  Gly  Gly  Asn  Gly  Gly  Gln  Gln  Gln  Lys  Phe  Met  Ala
                    100                      105                     110

Leu  Gly  Ser  Gly  Val  Ile  Ile  Asp  Ala  Asp  Lys  Gly  Tyr  Val  Val  Thr
               115                      120                     125

Asn  Asn  His  Val  Val  Asp  Asn  Ala  Thr  Val  Ile  Lys  Val  Gln  Leu  Ser
     130                      135                     140

Asp  Gly  Arg  Lys  Phe  Asp  Ala  Lys  Met  Val  Gly  Lys  Asp  Pro  Arg  Ser
145                      150                      155                     160

Asp  Ile  Ala  Leu  Ile  Gln  Ile  Gln  Asn  Pro  Lys  Asn  Leu  Thr  Ala  Ile
                    165                      170                     175

Lys  Met  Ala  Asp  Ser  Asp  Ala  Leu  Arg  Val  Gly  Asp  Tyr  Thr  Val  Gly
               180                      185                     190

Ile  Gly  Asn  Pro  Phe  Gly  Leu  Gly  Glu  Thr  Val  Thr  Ser  Gly  Ile  Val
               195                      200                     205

Ser  Ala  Leu  Gly  Arg  Ser  Gly  Leu  Asn  Ala  Glu  Asn  Tyr  Glu  Asn  Phe
     210                      215                      220

Ile  Gln  Thr  Asp  Ala  Ala  Ile  Asn  Arg  Gly  Asn  Ser  Gly  Gly  Ala  Leu
225                      230                      235                     240

Val  Asn  Leu  Asn  Gly  Glu  Leu  Ile  Gly  Ile  Asn  Thr  Ala  Ile  Leu  Ala
                    245                      250                     255

Pro  Asp  Gly  Gly  Asn  Ile  Gly  Ile  Gly  Phe  Ala  Ile  Pro  Ser  Asn  Met
                    260                      265                     270

Val  Lys  Asn  Leu  Thr  Ser  Gln  Met  Val  Glu  Tyr  Gly  Gln  Val  Lys  Arg
               275                      280                     285

Gly  Glu  Leu  Gly  Ile  Met  Gly  Thr  Glu  Leu  Asn  Ser  Glu  Leu  Ala  Lys
     290                      295                      300

Ala  Met  Lys  Val  Asp  Ala  Gln  Arg  Gly  Ala  Phe  Val  Ser  Gln  Val  Leu
305                      310                      315                     320

Pro  Asn  Ser  Ser  Ala  Ala  Lys  Ala  Gly  Ile  Lys  Ala  Gly  Asp  Val  Ile
                    325                      330                     335
```

```
Thr  Ser  Leu  Asn  Gly  Lys  Pro  Ile  Ser  Ser  Phe  Ala  Ala  Leu  Arg  Ala
               340                      345                350

Gln  Val  Gly  Thr  Met  Pro  Val  Gly  Ser  Lys  Leu  Thr  Leu  Gly  Leu  Leu
          355                      360                365

Arg  Asp  Gly  Lys  Gln  Val  Asn  Val  Asn  Leu  Glu  Leu  Gln  Gln  Ser  Ser
     370                      375                     380

Gln  Asn  Gln  Val  Asp  Ser  Ser  Ile  Phe  Asn  Gly  Ile  Glu  Gly  Ala
385                      390                     395                          400

Glu  Met  Ser  Asn  Lys  Gly  Lys  Asp  Gln  Gly  Val  Val  Val  Asn  Asn  Val
               405                      410                          415

Lys  Thr  Gly  Thr  Pro  Ala  Ala  Gln  Ile  Gly  Leu  Lys  Lys  Gly  Asp  Val
               420                      425                     430

Ile  Ile  Gly  Ala  Asn  Gln  Ile  Ala  Val  Lys  Asn  Ile  Ala  Glu  Ile  Arg
          435                      440                     445

Lys  Val  Leu  Asp  Ser  Lys  Pro  Ser  Val  Leu  Ala  Leu  Asn  Ile  Gln  Arg
     450                      455                     460

Gly  Asp  Arg  His  Leu  Pro  Val  Asn
465                      470
```

( 2 ) INFORMATION FOR SEQ ID NO:6:

( i ) SEQUENCE CHARACTERISTICS:
        ( A ) LENGTH: 475 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Met  Lys  Lys  Thr  Thr  Leu  Ala  Met  Ser  Ala  Leu  Ala  Leu  Ser  Leu  Gly
1                   5                     10                          15

Leu  Ala  Leu  Ser  Pro  Leu  Ser  Ala  Thr  Ala  Ala  Glu  Thr  Ser  Ser  Ser
               20                      25                     30

Ala  Met  Thr  Ala  Gln  Gln  Met  Pro  Ser  Leu  Ala  Pro  Met  Leu  Glu  Lys
          35                      40                     45

Val  Met  Pro  Ser  Val  Val  Ser  Ile  Asn  Val  Glu  Gly  Ser  Thr  Thr  Val
     50                      55                     60

Asn  Thr  Pro  Arg  Met  Pro  Arg  Asn  Phe  Gln  Gln  Phe  Phe  Gly  Asp  Asp
65                       70                      75                           80

Ser  Pro  Phe  Cys  Gln  Asp  Gly  Ser  Pro  Phe  Gln  Asn  Ser  Pro  Phe  Cys
               85                      90                          95

Gln  Gly  Gly  Gly  Asn  Gly  Gly  Asn  Gly  Gly  Gln  Gln  Gln  Lys  Phe  Met
               100                     105                     110

Ala  Leu  Gly  Ser  Gly  Val  Ile  Ile  Asp  Ala  Asp  Lys  Gly  Tyr  Val  Val
          115                     120                     125

Thr  Asn  Asn  His  Val  Val  Asp  Asn  Ala  Ser  Val  Ile  Lys  Val  Gln  Leu
     130                     135                     140

Ser  Asp  Gly  Arg  Lys  Phe  Asp  Ala  Lys  Val  Val  Gly  Lys  Asp  Pro  Arg
145                      150                     155                          160

Ser  Asp  Ile  Ala  Leu  Ile  Gln  Ile  Gln  Asn  Pro  Lys  Asn  Leu  Thr  Ala
               165                     170                     175

Ile  Lys  Leu  Ala  Asp  Ser  Asp  Ala  Leu  Arg  Val  Gly  Asp  Tyr  Thr  Val
               180                     185                     190

Ala  Ile  Gly  Asn  Pro  Phe  Gly  Leu  Gly  Glu  Thr  Val  Thr  Ser  Gly  Ile
          195                     200                     205

Val  Ser  Ala  Leu  Gly  Arg  Ser  Gly  Leu  Asn  Val  Glu  Asn  Tyr  Glu  Asn
     210                     215                     220
```

```
Phe Ile Gln Thr Asp Ala Ala Ile Asn Arg Gly Asn Ser Gly Gly Ala
225                 230                 235                 240

Leu Val Asn Leu Asn Gly Glu Leu Ile Gly Ile Asn Thr Ala Ile Leu
                245                 250                 255

Ala Pro Asp Gly Gly Asn Ile Gly Ile Gly Phe Ala Ile Pro Ser Asn
            260                 265                 270

Met Val Lys Asn Leu Thr Ser Gln Met Val Glu Tyr Gly Gln Val Arg
            275                 280                 285

Arg Gly Glu Leu Gly Ile Met Gly Thr Glu Leu Asn Ser Glu Leu Ala
    290                 295                 300

Lys Ala Met Lys Val Asp Ala Gln Arg Gly Ala Phe Val Ser Gln Val
305                 310                 315                 320

Met Pro Asn Ser Ser Ala Ala Lys Ala Gly Ile Lys Ala Gly Asp Val
                325                 330                 335

Ile Thr Ser Leu Asn Gly Lys Pro Ile Ser Ser Phe Ala Ala Leu Arg
                340                 345                 350

Ala Gln Val Gly Thr Met Pro Val Gly Ser Lys Ile Ser Leu Gly Leu
            355                 360                 365

Leu Arg Glu Gly Lys Ala Ile Thr Val Asn Leu Glu Leu Gln Gln Ser
    370                 375                 380

Ser Gln Ser Gln Val Asp Ser Ser Thr Ile Phe Ser Gly Ile Glu Gly
385                 390                 395                 400

Ala Glu Met Ser Asn Lys Gly Gln Asp Lys Gly Val Val Val Ser Ser
                405                 410                 415

Val Lys Ala Asn Ser Pro Ala Ala Gln Ile Gly Leu Lys Lys Gly Asp
            420                 425                 430

Val Ile Ile Gly Ala Asn Gln Ile Pro Val Lys Asn Ile Ala Glu Ile
        435                 440                 445

Arg Lys Ile Leu Asp Ser Lys Pro Ser Val Leu Ala Leu Asn Ile Gln
450                 455                 460

Arg Gly Asp Ser Ser Ile Tyr Leu Leu Met Gln
465                 470                 475
```

(2) INFORMATION FOR SEQ ID NO:7:

(i) SEQUENCE CHARACTERISTICS:
(A) LENGTH: 228 amino acids
(B) TYPE: amino acid
(C) STRANDEDNESS: single
(D) TOPOLOGY: linear (xi) SEQUENCE DESCRIPTION: SEQ ID NO:7:

```
Ile Val Gly Gly Tyr Lys Cys Glu Lys Asn Ser Gln Pro Trp Gln Val
1               5                   10                  15

Ala Val Ile Asn Glu Tyr Leu Cys Gly Gly Val Leu Ile Asp Pro Ser
            20                  25                  30

Trp Val Ile Thr Ala Ala His Cys Tyr Ser Asn Asn Tyr Gln Val Leu
            35                  40                  45

Leu Gly Arg Asn Asn Leu Phe Lys Asp Glu Pro Phe Ala Gln Arg Arg
    50                  55                  60

Leu Val Pro Gln Ser Phe Arg His Pro Asp Tyr Ile Pro Leu Ile Pro
65                  70                  75                  80

Val His Asp His Ser Asn Asp Leu Met Leu Leu His Leu Ser Glu Pro
                85                  90                  95

Ala Asp Ile Thr Gly Gly Val Lys Val Ile Asp Leu Pro Thr Lys Glu
            100                 105                 110
```

```
    Pro  Lys  Val  Gly  Ser  Thr  Cys  Leu  Ala  Ser  Gly  Trp  Gly  Ser  Thr  Asn
         115                      120                           125

Pro  Ser  Glu  Met  Val  Val  Ser  His  Asp  Leu  Gln  Cys  Val  Asn  Ile  His
         130                      135                           140

Leu  Leu  Ser  Asn  Glu  Lys  Cys  Ile  Glu  Thr  Tyr  Lys  Asp  Asn  Val  Thr
    145                           150                      155                    160

Asp  Val  Met  Leu  Cys  Ala  Gly  Glu  Met  Glu  Gly  Gly  Lys  Asp  Thr  Cys
                        165                      170                      175

Ala  Gly  Asp  Ser  Gly  Gly  Pro  Leu  Ile  Cys  Asp  Gly  Val  Leu  Gln  Gly
                   180                      185                           190

Ile  Thr  Ser  Gly  Gly  Ala  Thr  Pro  Cys  Ala  Lys  Pro  Lys  Thr  Pro  Ala
              195                      200                      205

Ile  Tyr  Ala  Lys  Leu  Ile  Lys  Phe  Thr  Ser  Trp  Ile  Lys  Lys  Val  Met
         210                      215                           220

Lys  Glu  Asn  Pro
    225
```

( 2 ) INFORMATION FOR SEQ ID NO:8:

( i ) SEQUENCE CHARACTERISTICS:
        ( A ) LENGTH: 232 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

```
    Ile  Ile  Gly  Gly  Arg  Glu  Cys  Glu  Lys  Asn  Ser  His  Pro  Trp  Gln  Val
    1              5                        10                           15

Ala  Ile  Tyr  His  Tyr  Ser  Ser  Phe  Gln  Cys  Gly  Gly  Val  Leu  Val  Asn
                   20                      25                           30

Pro  Lys  Trp  Val  Leu  Thr  Ala  Ala  His  Cys  Lys  Asn  Asp  Asn  Tyr  Glu
              35                           40                      45

Val  Trp  Leu  Gly  Arg  His  Asn  Leu  Phe  Glu  Asn  Glu  Asn  Thr  Ala  Gln
         50                      55                           60

Phe  Phe  Gly  Val  Thr  Ala  Asp  Phe  Pro  His  Pro  Gly  Phe  Asn  Leu  Ser
    65                       70                           75                      80

Ala  Asp  Gly  Lys  Asp  Tyr  Ser  His  Asp  Leu  Met  Leu  Leu  Arg  Leu  Gln
                        85                      90                           95

Ser  Pro  Ala  Lys  Ile  Thr  Asp  Ala  Val  Lys  Val  Leu  Glu  Leu  Pro  Thr
                   100                     105                          110

Gln  Glu  Pro  Glu  Leu  Gly  Ser  Thr  Cys  Glu  Ala  Ser  Gly  Trp  Gly  Ser
              115                     120                          125

Ile  Glu  Pro  Gly  Pro  Asp  Asp  Phe  Glu  Phe  Pro  Asp  Glu  Ile  Gln  Cys
         130                     135                          140

Val  Gln  Leu  Thr  Leu  Leu  Gln  Asn  Thr  Phe  Cys  Ala  Asp  Ala  His  Pro
    145                      150                          155                     160

Asp  Lys  Val  Thr  Glu  Ser  Met  Leu  Cys  Ala  Gly  Tyr  Leu  Pro  Gly  Gly
                        165                     170                          175

Lys  Asp  Thr  Cys  Met  Gly  Asp  Ser  Gly  Gly  Pro  Leu  Ile  Cys  Asn  Gly
                   180                     185                          190

Met  Trp  Gln  Gly  Ile  Thr  Ser  Trp  Gly  His  Thr  Pro  Cys  Gly  Ser  Ala
              195                     200                          205

Asn  Lys  Pro  Ser  Ile  Tyr  Thr  Lys  Leu  Ile  Phe  Tyr  Leu  Asp  Trp  Ile
         210                     215                          220

Asp  Asp  Thr  Ile  Thr  Glu  Asn  Pro
    225                     230
```

( 2 ) INFORMATION FOR SEQ ID NO:9:

( i ) SEQUENCE CHARACTERISTICS:
        ( A ) LENGTH: 223 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
Ile Val Gly Gly Tyr Thr Cys Gly Ala Asn Thr Val Pro Tyr Gln Val
 1               5                  10                  15

Ser Leu Asn Ser Gly Tyr His Phe Cys Gly Gly Ser Leu Ile Asn Ser
            20                  25                  30

Gln Trp Val Val Ser Ala Ala His Cys Tyr Lys Ser Gly Ile Gln Val
        35                  40                  45

Arg Leu Gly Glu Asp Asn Ile Asn Val Val Glu Gly Asn Glu Gln Phe
    50                  55                  60

Ile Ser Ala Ser Lys Ser Ile Val His Pro Ser Tyr Asn Ser Asn Thr
65                  70                  75                  80

Leu Asn Asn Asp Ile Met Leu Ile Lys Leu Lys Ser Ala Ala Ser Leu
                85                  90                  95

Asn Ser Arg Val Ala Ser Ile Ser Leu Pro Thr Ser Cys Ala Ser Ala
            100                 105                 110

Gly Thr Gln Cys Leu Ile Ser Gly Trp Gly Asn Thr Lys Ser Ser Gly
        115                 120                 125

Thr Ser Tyr Pro Asp Val Leu Lys Cys Leu Lys Ala Pro Ile Leu Ser
    130                 135                 140

Asp Ser Ser Cys Lys Ser Ala Tyr Pro Gly Gln Ile Thr Ser Asn Met
145                 150                 155                 160

Phe Cys Ala Gly Tyr Leu Glu Gly Gly Lys Asp Ser Cys Gln Gly Asp
                165                 170                 175

Ser Gly Gly Pro Val Val Cys Ser Gly Lys Leu Gln Gly Ile Val Ser
            180                 185                 190

Trp Gly Ser Gly Cys Ala Gln Lys Asn Lys Pro Gly Val Tyr Thr Lys
        195                 200                 205

Val Cys Asn Tyr Val Ser Trp Ile Lys Gln Thr Ile Ala Ser Asn
    210                 215                 220
```

( 2 ) INFORMATION FOR SEQ ID NO:10:

( i ) SEQUENCE CHARACTERISTICS:
        ( A ) LENGTH: 228 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

```
Ile Val Asn Gly Glu Glu Ala Val Pro Gly Ser Trp Pro Trp Gln Val
 1               5                  10                  15

Ser Leu Gln Asp Lys Thr Gly Phe His Phe Cys Gly Gly Ser Leu Ile
            20                  25                  30

Asn Glu Asn Trp Val Val Thr Ala Ala His Cys Gly Val Thr Thr Ser
        35                  40                  45

Asp Val Val Val Ala Gly Glu Phe Asp Gln Gly Ser Ser Ser Glu Lys
    50                  55                  60

Ile Gln Lys Leu Lys Ile Ala Lys Val Phe Lys Asn Ser Lys Tyr Asn
65                  70                  75                  80
```

```
Ser  Leu  Thr  Ile  Asn  Asn  Asp  Ile  Thr  Leu  Leu  Lys  Leu  Ser  Thr  Ala
               85                      90                       95

Ala  Ser  Phe  Ser  Gln  Thr  Val  Ser  Ala  Val  Cys  Leu  Pro  Ser  Ala  Ser
              100                     105                      110

Asp  Asp  Phe  Ala  Ala  Gly  Thr  Thr  Cys  Val  Thr  Thr  Gly  Trp  Gly  Leu
          115                     120                      125

Thr  Arg  Tyr  Ala  Asn  Thr  Pro  Asp  Arg  Leu  Gln  Gln  Ala  Ser  Leu  Pro
     130                      135                     140

Leu  Leu  Ser  Asn  Thr  Asn  Cys  Lys  Lys  Tyr  Trp  Gly  Thr  Lys  Ile  Lys
145                      150                     155                           160

Asp  Ala  Met  Ile  Cys  Ala  Gly  Ala  Ser  Gly  Val  Ser  Ser  Cys  Met  Gly
               165                      170                      175

Asp  Ser  Gly  Gly  Pro  Leu  Val  Cys  Lys  Lys  Asn  Gly  Ala  Trp  Thr  Leu
               180                     185                      190

Val  Gly  Ile  Val  Ser  Trp  Gly  Ser  Ser  Thr  Cys  Ser  Thr  Ser  Thr  Pro
               195                     200                      205

Gly  Val  Tyr  Ala  Arg  Val  Thr  Ala  Leu  Val  Asn  Trp  Val  Gln  Gln  Thr
     210                      215                     220

Leu  Ala  Ala  Asn
225
```

(2) INFORMATION FOR SEQ ID NO:11:

(i) SEQUENCE CHARACTERISTICS:
        (A) LENGTH: 240 amino acids
        (B) TYPE: amino acid
        (C) STRANDEDNESS: single
        (D) TOPOLOGY: linear (xi) SEQUENCE DESCRIPTION: SEQ ID NO:11:

```
Val  Val  Gly  Gly  Thr  Glu  Ala  Gln  Arg  Asn  Ser  Trp  Pro  Ser  Gln  Ile
1               5                      10                       15

Ser  Leu  Gln  Tyr  Arg  Ser  Gly  Ser  Ser  Trp  Ala  His  Thr  Cys  Gly  Gly
               20                      25                       30

Thr  Leu  Ile  Arg  Gln  Asn  Trp  Val  Met  Thr  Ala  Ala  His  Cys  Val  Asp
          35                      40                       45

Arg  Glu  Leu  Thr  Phe  Arg  Val  Val  Gly  Glu  His  Asn  Leu  Asn  Gln
     50                      55                      60

Asn  Asn  Gly  Thr  Glu  Gln  Tyr  Val  Gly  Val  Gln  Lys  Ile  Val  Val  His
65                       70                      75                            80

Pro  Tyr  Trp  Asn  Thr  Asp  Asp  Val  Ala  Ala  Gly  Tyr  Asp  Ile  Ala  Leu
               85                      90                       95

Leu  Arg  Leu  Ala  Gln  Ser  Val  Thr  Leu  Asn  Ser  Tyr  Val  Gln  Leu  Gly
              100                     105                      110

Val  Leu  Pro  Arg  Ala  Gly  Thr  Ile  Leu  Ala  Asn  Asn  Ser  Pro  Cys  Tyr
              115                     120                      125

Ile  Thr  Gly  Trp  Gly  Leu  Thr  Arg  Thr  Asn  Gly  Gln  Leu  Ala  Gln  Thr
     130                      135                     140

Leu  Gln  Gln  Ala  Tyr  Leu  Pro  Thr  Val  Asp  Tyr  Ala  Ile  Cys  Ser  Ser
145                      150                     155                           160

Ser  Ser  Tyr  Trp  Gly  Ser  Thr  Val  Lys  Asn  Ser  Met  Val  Cys  Ala  Gly
               165                     170                      175

Gly  Asp  Gly  Val  Arg  Ser  Gly  Cys  Gln  Gly  Asp  Ser  Gly  Gly  Pro  Leu
               180                     185                      190

His  Cys  Leu  Val  Asn  Gly  Gln  Tyr  Ala  Val  His  Gly  Val  Thr  Ser  Phe
               195                     200                      205
```

```
        Val   Ser   Arg   Leu   Gly   Cys   Asn   Val   Thr   Arg   Lys   Pro   Thr   Val   Phe   Thr
              210                     215                           220

Arg   Val   Ser   Ala   Tyr   Ile   Ser   Trp   Ile   Asn   Asn   Val   Ile   Ala   Ser   Asn
        225                           230                           235                           240
```

( 2 ) INFORMATION FOR SEQ ID NO:12:

( i ) SEQUENCE CHARACTERISTICS:
        ( A ) LENGTH: 224 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

```
        Ile   Ile   Gly   Gly   Val   Glu   Ser   Ile   Pro   His   Ser   Arg   Pro   Tyr   Met   Ala
        1                       5                             10                            15

His   Leu   Asp   Ile   Val   Thr   Glu   Lys   Gly   Leu   Arg   Val   Ile   Cys   Gly   Gly
                          20                          25                          30

Phe   Leu   Ile   Ser   Arg   Gln   Phe   Val   Leu   Thr   Ala   Ala   His   Cys   Lys   Gly
                          35                          40                          45

Arg   Glu   Ile   Thr   Val   Ile   Leu   Gly   Ala   His   Asp   Val   Arg   Lys   Arg   Glu
              50                            55                            60

Ser   Thr   Gln   Gln   Lys   Ile   Lys   Val   Glu   Lys   Gln   Ile   Ile   His   Glu   Ser
        65                            70                            75                            80

Tyr   Asn   Ser   Val   Pro   Asn   Leu   His   Asp   Ile   Met   Leu   Leu   Lys   Leu   Glu
                                85                            90                            95

Lys   Lys   Val   Glu   Leu   Thr   Pro   Ala   Val   Asn   Val   Val   Pro   Leu   Pro   Ser
                          100                         105                         110

Pro   Ser   Asp   Phe   Ile   His   Pro   Gly   Ala   Met   Cys   Trp   Ala   Ala   Gly   Trp
                          115                         120                         125

Gly   Lys   Thr   Gly   Val   Arg   Asp   Pro   Thr   Ser   Tyr   Thr   Leu   Arg   Glu   Val
                          130                         135                         140

Glu   Leu   Arg   Ile   Met   Asp   Glu   Lys   Ala   Cys   Val   Asp   Tyr   Arg   Tyr   Tyr
        145                           150                           155                           160

Glu   Tyr   Lys   Phe   Gln   Val   Cys   Val   Gly   Ser   Pro   Thr   Thr   Leu   Arg   Ala
                                165                           170                           175

Ala   Phe   Met   Gly   Asp   Ser   Gly   Gly   Pro   Leu   Leu   Cys   Ala   Gly   Val   Ala
                          180                         185                         190

His   Gly   Ile   Val   Ser   Tyr   Gly   His   Pro   Asp   Ala   Lys   Pro   Pro   Ala   Ile
                          195                         200                         205

Phe   Thr   Arg   Val   Ser   Thr   Tyr   Val   Pro   Trp   Ile   Asn   Ala   Val   Ile   Asn
                    210                         215                         220
```

( 2 ) INFORMATION FOR SEQ ID NO:13:

( i ) SEQUENCE CHARACTERISTICS:
        ( A ) LENGTH: 223 amino acids
        ( B ) TYPE: amino acid
        ( C ) STRANDEDNESS: single
        ( D ) TOPOLOGY: linear ( x i ) SEQUENCE DESCRIPTION: SEQ ID NO:13:

```
        Val   Val   Gly   Gly   Thr   Arg   Ala   Ala   Gln   Gly   Glu   Phe   Pro   Phe   Met   Val
        1                       5                             10                            15

Arg   Leu   Ser   Met   Gly   Cys   Gly   Gly   Ala   Leu   Tyr   Ala   Gln   Asp   Ile   Val
                          20                          25                          30

Leu   Thr   Ala   Ala   His   Cys   Val   Ser   Gly   Ser   Gly   Asn   Asn   Thr   Ser   Ile
                    35                          40                          45

Thr   Ala   Thr   Gly   Gly   Val   Val   Asp   Leu   Gln   Ser   Gly   Ala   Ala   Val   Lys
```

```
                  50                        55                          60
   Val  Arg  Ser  Thr  Lys  Val  Leu  Gln  Ala  Pro  Gly  Tyr  Asn  Gly  Thr  Gly
   65                       70                       75                       80

Lys  Asp  Trp  Ala  Leu  Ile  Lys  Leu  Ala  Gln  Pro  Ile  Asn  Gln  Pro  Thr
                            85                       90                       95

Leu  Lys  Ile  Ala  Thr  Thr  Thr  Ala  Tyr  Asn  Gln  Gly  Thr  Phe  Thr  Val
                       100                      105                      110

Ala  Gly  Trp  Gly  Ala  Asn  Arg  Glu  Gly  Gly  Ser  Gln  Gln  Arg  Tyr  Leu
                  115                      120                      125

Leu  Lys  Ala  Asn  Val  Pro  Phe  Val  Ser  Asp  Ala  Ala  Cys  Arg  Ser  Ala
             130                      135                      140

Tyr  Gly  Asn  Glu  Leu  Val  Ala  Asn  Glu  Glu  Ile  Cys  Ala  Gly  Tyr  Pro
   145                      150                      155                      160

Asp  Thr  Gly  Gly  Val  Asp  Thr  Cys  Gln  Gly  Asp  Ser  Gly  Gly  Pro  Met
                            165                      170                      175

Phe  Arg  Lys  Asp  Asn  Ala  Asp  Glu  Trp  Ile  Gln  Val  Gly  Ile  Val  Ser
                       180                      185                      190

Trp  Gly  Tyr  Gly  Cys  Ala  Arg  Pro  Gly  Tyr  Pro  Gly  Val  Tyr  Thr  Glu
                  195                      200                      205

Val  Ser  Thr  Phe  Ala  Ser  Ala  Ile  Ala  Ser  Ala  Ala  Arg  Thr  Leu
             210                      215                      220
```

( 2 ) INFORMATION FOR SEQ ID NO:14:

( i ) SEQUENCE CHARACTERISTICS:
        ( A ) LENGTH: 185 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

```
   Ile  Ser  Gly  Gly  Asp  Ala  Ile  Tyr  Ser  Ser  Thr  Gly  Arg  Cys  Ser  Leu
   1                   5                        10                       15

Gly  Phe  Asn  Val  Arg  Ser  Gly  Ser  Thr  Tyr  Tyr  Phe  Leu  Thr  Ala  Gly
                       20                       25                       30

His  Cys  Thr  Asp  Gly  Ala  Thr  Thr  Trp  Trp  Ala  Asn  Ser  Ala  Arg  Thr
             35                       40                       45

Thr  Val  Leu  Gly  Thr  Thr  Ser  Gly  Ser  Ser  Phe  Pro  Asn  Asn  Asp  Tyr
        50                       55                       60

Gly  Ile  Val  Arg  Tyr  Thr  Asn  Thr  Thr  Ile  Pro  Lys  Asp  Gly  Thr  Val
   65                       70                       75                       80

Gly  Gly  Gln  Asp  Ile  Thr  Ser  Ala  Ala  Asn  Ala  Thr  Val  Gly  Met  Ala
                       85                       90                       95

Val  Thr  Arg  Arg  Gly  Ser  Thr  Thr  Gly  Thr  His  Ser  Gly  Ser  Val  Thr
                  100                      105                      110

Ala  Leu  Asn  Ala  Thr  Val  Asn  Tyr  Gly  Gly  Gly  Asp  Val  Val  Tyr  Gly
             115                      120                      125

Met  Ile  Arg  Thr  Asn  Val  Cys  Ala  Glu  Pro  Gly  Asp  Ser  Gly  Gly  Pro
        130                      135                      140

Leu  Tyr  Ser  Gly  Thr  Arg  Ala  Ile  Gly  Leu  Thr  Ser  Gly  Gly  Ser  Gly
   145                      150                      155                      160

Asn  Cys  Ser  Ser  Gly  Gly  Thr  Thr  Phe  Phe  Gln  Pro  Val  Thr  Glu  Ala
                       165                      170                      175

Leu  Val  Ala  Tyr  Gly  Val  Ser  Val  Tyr
                  180                      185
```

( 2 ) INFORMATION FOR SEQ ID NO:15:

( i ) SEQUENCE CHARACTERISTICS:
        ( A ) LENGTH: 181 amino acids
        ( B ) TYPE: amino acid
        ( C ) STRANDEDNESS: single
        ( D ) TOPOLOGY: linear ( x i ) SEQUENCE DESCRIPTION: SEQ ID NO:15:

```
Ile Ala Gly Gly Glu Ala Ile Thr Thr Gly Gly Ser Arg Cys Ser Leu
 1               5                  10                  15
Gly Phe Asn Val Ser Val Asn Gly Val Ala His Ala Leu Thr Ala Gly
                20                  25                  30
His Cys Thr Asn Ile Ser Ala Ser Trp Ser Ile Gly Thr Arg Thr Gly
            35                  40                  45
Thr Ser Phe Pro Asn Asn Asp Tyr Gly Ile Ile Arg His Ser Asn Pro
        50                  55                  60
Ala Ala Ala Asp Gly Arg Val Tyr Leu Tyr Asn Gly Ser Tyr Gln Asp
65                  70                  75                  80
Ile Thr Thr Ala Gly Asn Ala Phe Val Gly Gln Ala Val Gln Arg Ser
                85                  90                  95
Gly Ser Thr Thr Gly Leu Arg Ser Gly Ser Val Thr Gly Leu Asn Ala
                100                 105                 110
Thr Val Asn Tyr Gly Ser Ser Gly Ile Val Tyr Gly Met Ile Gln Thr
            115                 120                 125
Asn Val Cys Ala Gln Pro Gly Asp Ser Gly Gly Ser Leu Phe Ala Gly
        130                 135                 140
Ser Thr Ala Leu Gly Leu Thr Ser Gly Gly Ser Gly Asn Cys Arg Thr
145                 150                 155                 160
Gly Gly Thr Thr Phe Tyr Gln Pro Val Thr Glu Ala Leu Ser Ala Tyr
                165                 170                 175
Gly Ala Thr Val Leu
                180
```

( 2 ) INFORMATION FOR SEQ ID NO:16:

( i ) SEQUENCE CHARACTERISTICS:
        ( A ) LENGTH: 198 amino acids
        ( B ) TYPE: amino acid
        ( C ) STRANDEDNESS: single
        ( D ) TOPOLOGY: linear ( x i ) SEQUENCE DESCRIPTION: SEQ ID NO:16:

```
Ala Asn Ile Val Gly Gly Ile Glu Tyr Ser Ile Asn Asn Ala Ser Leu
 1               5                  10                  15
Cys Ser Val Gly Phe Ser Val Thr Arg Gly Ala Thr Lys Gly Phe Val
                20                  25                  30
Thr Ala Gly His Cys Gly Thr Val Asn Ala Thr Ala Arg Ile Gly Gly
            35                  40                  45
Ala Val Val Gly Thr Phe Ala Ala Arg Val Phe Pro Gly Asn Asp Arg
        50                  55                  60
Ala Trp Val Ser Leu Thr Ser Ala Gln Thr Leu Leu Pro Arg Val Ala
65                  70                  75                  80
Asn Gly Ser Ser Phe Val Thr Val Arg Gly Ser Thr Glu Ala Ala Val
                85                  90                  95
Gly Ala Ala Val Cys Arg Ser Gly Arg Thr Thr Gly Tyr Gln Cys Gly
                100                 105                 110
Thr Ile Thr Ala Lys His Val Thr Ala Asn Tyr Ala Glu Gly Ala Val
            115                 120                 125
```

```
        Arg  Gly  Leu  Thr  Gln  Gly  Asn  Ala  Cys  Met  Gly  Arg  Gly  Asp  Ser  Gly
             130                 135                      140

Gly  Ser  Trp  Ile  Thr  Ser  Ala  Gly  Gln  Ala  Gln  Gly  Val  Met  Ser  Gly
        145                      150                      155                           160

Gly  Asn  Val  Gln  Ser  Asn  Gly  Asn  Asn  Cys  Gly  Ile  Pro  Ala  Ser  Gln
                            165                           170                 175

Arg  Ser  Ser  Leu  Phe  Glu  Arg  Leu  Gln  Pro  Ile  Leu  Ser  Gln  Tyr  Gly
                       180                      185                           190

Leu  Ser  Leu  Val  Thr  Gly
                       195
```

( 2 ) INFORMATION FOR SEQ ID NO:17:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:17:

```
        Gly  Asn  Ser  Gly  Gly  Ala  Leu
        1                   5
```

( 2 ) INFORMATION FOR SEQ ID NO:18:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( x i ) SEQUENCE DESCRIPTION: SEQ ID NO:18:

```
        Gly  Asp  Ser  Gly  Gly  Pro  Lys
        1                   5
```

( 2 ) INFORMATION FOR SEQ ID NO:19:

( i ) SEQUENCE CHARACTERISTICS:
    ( A ) LENGTH: 14 amino acids
    ( B ) TYPE: amino acid
    ( C ) STRANDEDNESS: single
    ( D ) TOPOLOGY: linear ( x i ) SEQUENCE DESCRIPTION: SEQ ID NO:19:

```
        Met  Lys  Lys  Thr  Arg  Phe  Val  Leu  Asn  Ser  Ile  Ala  Leu  Gly
        1                   5                        10
```

( 2 ) INFORMATION FOR SEQ ID NO:20:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

CGCTCCACCA GCATTACCGC GG                22

( 2 ) INFORMATION FOR SEQ ID NO:21:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

ATCAATAACA GCATTATTGG T                     21

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

TAATGCAATT GCTGATAGTT C                     21

( 2 ) INFORMATION FOR SEQ ID NO:23:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:23:

Lys Phe Phe Phe Gly Asp Arg Phe Ala Glu Gln
1               5                   10

ANALOG OF HAEMOPHILUS HIN47 WITH REDUCED PROTEASE ACTIVITY

FIELD OF THE INVENTION

The present invention relates to the field of immunology and is particularly concerned with immunogens and antigens from species of Haemophilus.

BACKGROUND OF THE INVENTION

*Haemophilus influenzae* is the organism responsible for a variety of serious human diseases, such as meningitis, epiglotitis, pneumonia and otitis media. *Haemophilus influenzae* type b (Hib) is a major cause of bacterial meningitis in children under the age of five years. Protective antibodies to the disease are induced by the capsular polysaccharide of the organism and vaccines have been developed that utilise the purified polyribosyl ribotol phosphate (PRP) as the antigen. This vaccine provides 90% protection in adults and in children over 24 months of age, but was ineffective in children under 24 months (Zangwill et al 1993) (The references are identified in a list of references at the end of this disclosure, each of which reference in the list is hereby incorporated by reference without further reference thereto). Like other polysaccharide antigens, PRP does not induce the proliferation of T-helper cells, and re-immunisation fails to elicit either a booster response or an increase in memory cells. Conjugation of the PRP polysaccharide with protein carriers confers T-cell dependent characteristics to the vaccine and substantially enhances the immunologic response to the PRP antigen. Currently, there are four PRP-carrier conjugate vaccines available. These are vaccines based upon *H. influenzae* type b capsular polysaccharide conjugated to diphtheria toxoid, tetanus toxoid, or *Neisseria meningitidis* outer membrane protein (reviewed in Zangwill et al 1993). These *H. influenzae* b conjugate vaccines have dramatically reduced the incidence of bacterial meningitis (Schoendorf et al., 1994).

There are six serotypes of *H. influenzae* designated a to f, which are defined by their capsular polysaccharides. The current Haemophilus conjugate vaccines do not protect against other invasive typable strains (types a and c) and, importantly, do not protect against non-typable (NTHi) strains which are a common cause of postpartum and neonatal sepsis, pneumonia and otitis media. Otitis media is the most common illness of early childhood with approximately 70% of all children suffering at least one bout of otitis media before the age of seven. Chronic otitis media can lead to hearing, speech, and cognitive impairment in children. It is caused by bacterial infection with *Streptococcus pneumoniae* (approximately 50%), non-typable *H. influenzae* (approximately 30%), and *Moraxella* (Branhamella) *catarrhalis* (approximately 20%). In the United States alone, treatment of otitis media costs between 1 and 2 billion dollars per year for antibiotics and surgical procedures, such as tonsillectomies, adenoidectomies and insertion of tympanostomy tubes. To achieve universal protection against *H. influenzae* related diseases, particularly in the two to six month age group and certain high risk groups, the provision of conserved, cross-reactive non-capsular *H. influenzae* immunogens is desirable. Non-typable strains of *H. influenzae* are also important pathogens responsible for pneumonia in the elderly and other individuals who are particularly susceptible to respiratory infections. There is thus a need for antigens from *H. influenzae* which are useful as components in immunogenic preparations that provide protection against the many serotypes of *H. influenzae*, PCT application WO 92/10936, published Jul. 9, 1992 and incorporated herein by reference thereto, describes a 47,000 molecular weight outer membrane protein obtained from *H. influenzae* that is reported to be an adhesin and has been termed Hin47 that is immunologically conserved between non-typable, type b and non-typed clinical isolates of *H. influenzae*. The amino acid sequence of Hin47 and the nucleotide sequence of the gene encoding Hin47 were presented at the American Society of Microbiology (ASM) conference held in New Orleans, May 26–30, 1992. These sequences have also been published in PCT application WO 94/00149, published Jan. 6, 1994 and incorporated herein by reference thereto.

Since Hin47 is conserved among strains of *Haemophilus influenzae*, and is reported to be an adhesin, the protein has utility in diagnosis of and vaccination against disease caused by *H. influenzae* or other bacterial pathogens that produce Hin47 or a protein capable of raising antibodies specifically reactive with Hin47.

A disadvantage of Hin47 for use as an antigen in diagnosis, for the generation of anti-Hin47 antibodies useful in diagnosis and as an immunogen in vaccination is the unexpected discovery by the present applicants that Hin47 has protease activity which results in the autodigestion of Hin47 and the proteolytic degradation of other antigens mixed therewith.

It would be advantageous to provide analogs of Hin47 protein (sometimes referred to herein as mutants or derivatives) that are substantially reduced in proteolytic activity for use as antigens, immunogenic preparations including vaccines, carriers for other immunogens and the generation of diagnostic reagents.

SUMMARY OF THE INVENTION

The present invention is directed towards the provision of analogs of Haemophilus Hin47 protein having reduced protease activity.

In accordance with one aspect of the invention there is provided an isolated and purified analog of *Haemophilus influenzae* Hin47 protein having a decreased protease activity which is less than about 10% of natural Hin47 protein. Such Hin47 analog preferably has substantially the same immunogenic properties of natural Hin47 protein. The analog of the present invention may be produced by chemical, biochemical or genetic modification of natural Hin47.

In one embodiment of the present invention, when the analog is produced by genetic modification, at least one amino acid of the natural Hin47 contributing to protease activity may be deleted or replaced by a different amino acid to produce the reduced protease activity. Alternatively, the reduced protease activity may be achieved by inserting at least one amino acid into the natural Hin47 protein. The at least one deleted or replaced amino acid may be selected from amino acids 195 to 201 of Hin47, and specifically may be Serine-197, which may be deleted or replaced by alanine. In addition, the at least one deleted or replaced amino acid may be His-91 and may be deleted or replaced by alanine or lysine or arginine. Further, the at least one deleted or replaced amino acid may be Asp-121 and may be deleted or replaced by alanine or glutamic acid.

In a further aspect, the present invention provides an isolated and purified nucleic acid molecule comprising a mutant *Haemophilus influenzae* hin47 gene encoding an analog of *Haemophilus influenzae* Hin47 protein having a reduced protease activity which is less than about 10% of natural Hin47 protein. The mutant hin47 gene may encode any of the Hin47 analogs discussed above. The mutant gene preferably is formed by site-directed mutagenesis of a wild-type hin47 gene. The nucleic acid molecule may be contained in a recombinant plasmid adapted for transformation of a host and may be plasmid DS-1011-1-1 (deposited on Jul. 27, 1994 at American type Culture Collection under Accession No. 75845. The invention also includes a transformed cell containing such a recombinant plasmid.

The present invention, in another aspect, includes a method for producing an analog of *Haemophilus influenzae* Hin47 protein having a reduced protease activity which is less than about 10% of natural Hin47 protein, which comprises identifying at least one amino acid residue of Hin47 protein which contributes to protease activity thereof, effecting site-directed mutagenesis of the hin47 gene to remove or replace a nucleotide sequence encoding the at least one amino acid and to produce a mutated hin47 gene, introducing the mutated hin47 gene into a cell to produce a transformed cell and growing the transformed cell to produce the Hin47 analog. The at least one amino acid which is selected may be any of the ones specifically identified above with respect to the Hin47 analog.

The introduction of the mutated hin47 gene preferably produces a transformed cell in which the mutated hin47 gene is under control of the T7 promoter and the growing of the transformed cell and expression of the Hin47 analog of the T7 promoter than preferably is effected by culturing in an inducing concentration of lactose. Preferably, the introduction of the mutated hin47 is effected by transforming the cell with the recombinant plasmid "DS-1011-1-1, sometimes otherwise referred to as plasmid" pT7/Hin47.

A further aspect of the invention provides a method of providing isolated and purified Hin47 analog, which comprises effecting the procedure described above for the production of the Hin47 analog to produce grown transformed cells harbouring inclusion bodies containing the Hin47 analog, disrupting the grown transformed cells to produce supernatant and the inclusion bodies, solubilizing the inclusion bodies to produce a solution containing Hin47 analog, chromatographically purifying the Hin47 analog from the solution free from cell debris, and isolating the purified Hin47 analog.

The analogs of Hin47 provided herein with their decreased proteolytic activity are useful as antigens in immunogenic composition, carriers for other immunogens, diagnostic agents and in the generation of diagnostic agents. The nucleic acid molecules also are useful as probes for diagnostic use and also as in immunogenic compositions.

In a further aspect of the invention, there is provided an immunogenic composition comprising an immuno-effective amount of the Hin47 analog or of the nucleic acid molecule including the gene encoding the Hin47 analog. The immunogenic composition may be formulated as a vaccine for in vivo administration to a host, including a human, to confer protection against diseases caused by a bacterial pathogen that produces Hin47 or a protein capable of inducing antibodies in the host specifically reactive with Hin47. The bacterial pathogen may be a Haemophilus species, such as *Haemophilus influenzae*. The immunogenic compositions of the invention may further comprise at least one other immunogenic or immunostimulating material, such as an adjuvant. In an additional embodiment, the nucleic acid molecule comprising a gene encoding the Hin47 analog may be contained within a live vector, such as a pox virus, Salmonella, poliovirus, adenovirus, vaccinia or BCG.

The invention also extends to a method of generating an immune response in a host, including a human, comprising administering thereto an immuno-effective amount of the immunogenic compositions provided herein.

As mentioned above, the Hin47 analog provided herein is useful in diagnostic applications. Accordingly, in an additional aspect of the invention, there is provided a method of determining the presence of antibodies specifically reactive with Hin47 in a sample, comprising the steps of:

(a) contacting the sample with the Hin47 analog having substantially the same immunogenic properties as the natural Hin47 protein as provided herein to produce complexes comprising the Hin47 analog and any such antibodies present in the sample specifically reactive therewith; and (b) determining the production of the complexes.

The present invention also provides a method of determining the presence of Hin47 in a sample, comprising the steps of:

(a) immunizing a subject with an immunogenic composition as provided herein to produce antibodies specific for Hin47 protein;

(b) contacting the sample with the antibodies to produce complexes comprising any Hin47 present in the sample and the Hin47 specific antibodies; and (c) determining production of the complexes.

The invention also extends to a diagnostic kit for determining the presence of antibodies in a sample specifically reactive with Hin47, comprising:

(a) the Hin47 analog having substantially the same immunogenic properties as the natural Hin47 protein as provided herein;

(b) means for contacting the analog with the sample to produce a complex comprising the analog and any such antibodies present in the sample; and (c) means for determining production of the complex.

BRIEF DESCRIPTION OF THE DRAWINGS

FIG. 2 shows the full nucleotide (SEQ ID NO: 1) and deduced amino acid sequence (SEQ ID NO: 2) of Hin47 from *H. influenzae* strain SB33 as well as a partial nucleotide sequence (SEQ ID NO: 3) and a partial deduced amino acid sequence (SEQ ID NO: 4) thereof, the latter being specifically copied by an inventor herein from materials presented in the ASM conference as described above;

FIG. 3 shows a comparison of the amino acid sequences of *H. influenzae* Hin47 (SEQ ID NO: 2), *E. coli* htrA (SEQ ID NO: 5), and *Salmonella typhimurium* htrA (SEQ ID NO: 6);

FIG. 4 shows an alignment of amino acid residues 57 to 256 of Hin47 with certain known proteases (SEQ ID NOS: 7 to 16). Codes are as follows: TON, rat tonin; PKAAB, kallikrein; PTN, trypsin; CHAA, chymotrypsin; EST, elastase; RP2A, rat mast cell protease; SGT, Streptomyces griseus trypsin; SGBE, S. griseus proteinase A; SGA, S. griseus proteinase B; ALP, L. enzymogenes alpha-lytic protease; hin47, res. 57–256 of Hin47. Asterisks (*) denote structurally conserved regions. The catalytic triad residues are indicated by a hash mark (#). 'con' refers to regions of structural concensus, among the mammalian proteases;

FIG. 10 shows the comparative immunogenicity of natural Hin47 and the Hin47 analog in mice.

GENERAL DESCRIPTION OF INVENTION

Any Haemophilus strains that have Hin47 genes may be conveniently used to provide the purified and isolated nucleic acid molecules (which may be in the form of DNA molecules), comprising at least a portion coding for Hin47 as typified by embodiments of the present invention. Such strains are generally available from clinical sources and from bacterial culture collections, such as the American Type Culture collection. Such strains include *H. influenzae* strains and other bacteria that produce a protein capable of generating antibodies that specifically recognize Hin47 fragment or analog thereof. Appropriate strains of Haemophilus may include:

*H. influenzae* type b strain MinnA;

*H. influenzae* type b strain Eagan;

*H. influenzae* non-typable strain SB33; or

*H. influenzae* non-typable strain PAK 12085.

Figure 1:
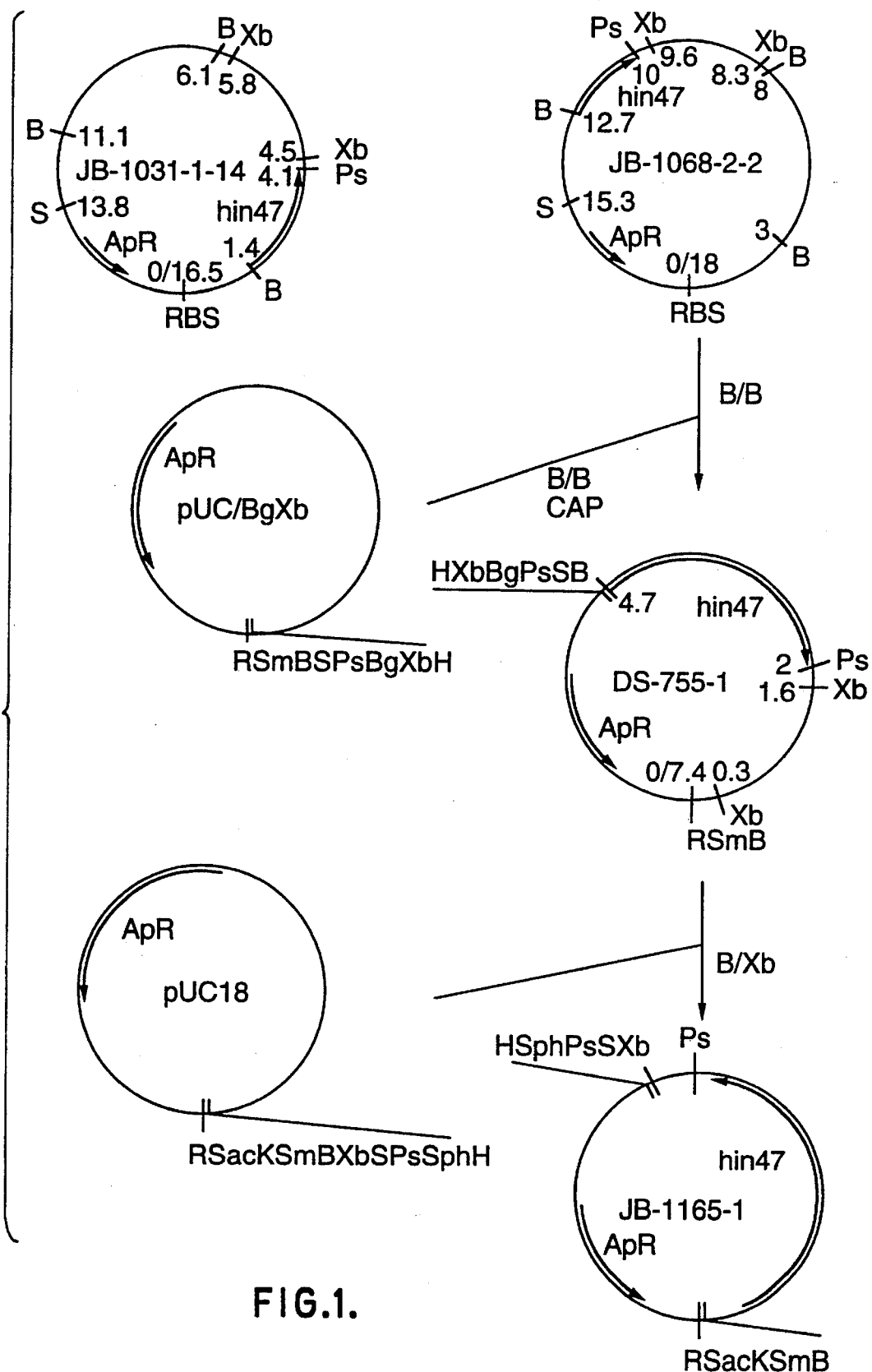
FIG. 1 shows the restriction maps of plasmids JB-1031-1-14 and JB-1068-2-2 -and the construction of the plasmids for sequence analysis.

Referring to FIG. 1, there is illustrated restriction maps of plasmids JB-1031-1-14 and JB-1068-2-2 that contain a portion encoding Hin47 protein from non-typable *H. influenzae* SB33. The nucleotide sequence of the Hin47 gene was determined and is shown in FIG. 2 along with the deduced amino acid sequence of the Hin47 protein. Referring to FIG. 3, there is shown an amino acid sequence alignment of *H. influenzae* Hin47 and the serine proteases htrA from *Escherichia coli* and htrA from *Salmonella typhimurium*. This alignment for the first time reveals the unexpected discovery of the present applicants that Hin47 is related to bacterial serine proteases and that Hin47 has protease activity. Hin47 has previously been reported to be an adhesin. The discovered protease activity thereof greatly limits the usefulness of natural Hin47 as an immunogen for vaccination and as an antigen in diagnostic uses. The sequence alignment shown in FIG. 3 revealed that the htrA proteins and Hin47 contain a GNSGGAL (SEQ ID NO: 17) sequence between residues 195 and 201 of the mature protein. The consensus sequence of the active site of serine proteases is GDSGGPK (SEQ ID NO: 18) (Brenner, 1988) and the active residue is serine. Thus, Serine-197 in Hin47 was mutated to produce an analog of Hin47 reduced in protease activity, in accordance with one embodiment of the invention. In a particular embodiment, Serine-197 was replaced by alanine. Amino acid residues 57 to 256 of Hin47 were further aligned with known proteases and the active site residues identified from the local homologies surrounding the residues of the catalytic triad (FIG. 4). There is a standard numbering system for serine proteases in which the catalytic triad residues are numbered as His-57, Asp-102 and Ser-195. These correspond to residues His-91, Asp-121 and Ser-197 in the sequential numbering system. Thus, referring to FIG. 4, there is shown a structure-based alignment of ten structurally determined serine proteases (SEQ ID NOS: 7 to 16) in which homologous residues are aligned primarily on the basis of similar locations in three-dimensional space. The location of many of the residues in the hydrophobic core of Hin47, as well as residues around the active site can be aligned reasonably well to identify functional amino acids of the Hin47 protease. Thus, other amino acid residues in Hin47 that contribute to protease activity of the protein include His-91 and Asp-121. In particular embodiments, His-91 may be replaced by alanine, lysine or arginine. In an additional embodiment, Asp-121 may be replaced by alanine or glutamic acid. Although the provision of an analog of Hin47 having reduced protease activity has been exemplified herein by particular amino acid substitution within Hin47 protein, the discovery of the protease activity and the methods of Hin47 expression, purification and analysis provided herein, allow for the production of other analogs having at least one other amino acid deleted or replaced or having at least one additional amino acid inserted into the Hin47 protein. In particular applications and embodiments, it may be desirable to simultaneously alter several amino acids of the Hin47 protein to particularly reduce the protease activity of Hin47. Accordingly, the present invention provides analogs of Hin47 protein having decreased protease activity due to single or multiple amino acid deletions, replacements or additions within the Hin47 protein.

Figure 5B:
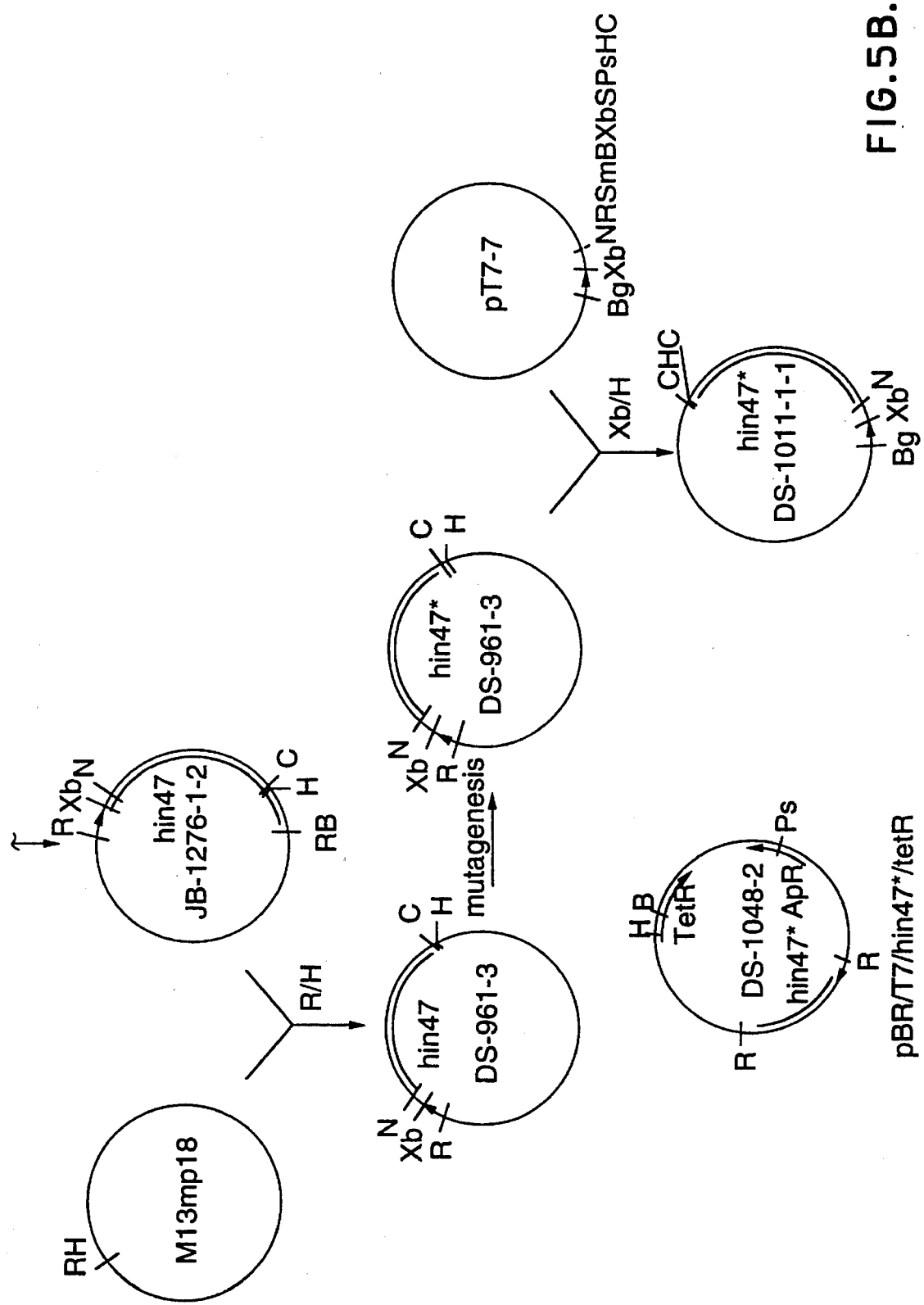
FIG. 5 shows the restriction maps for plasmids DS-1011-1-1 and DS-1048-2 which express a Hin47 analog from *E. coli* and a construction scheme for plasmid DS-1011-1-1 (pT7/Hin47*)
Figure 6:
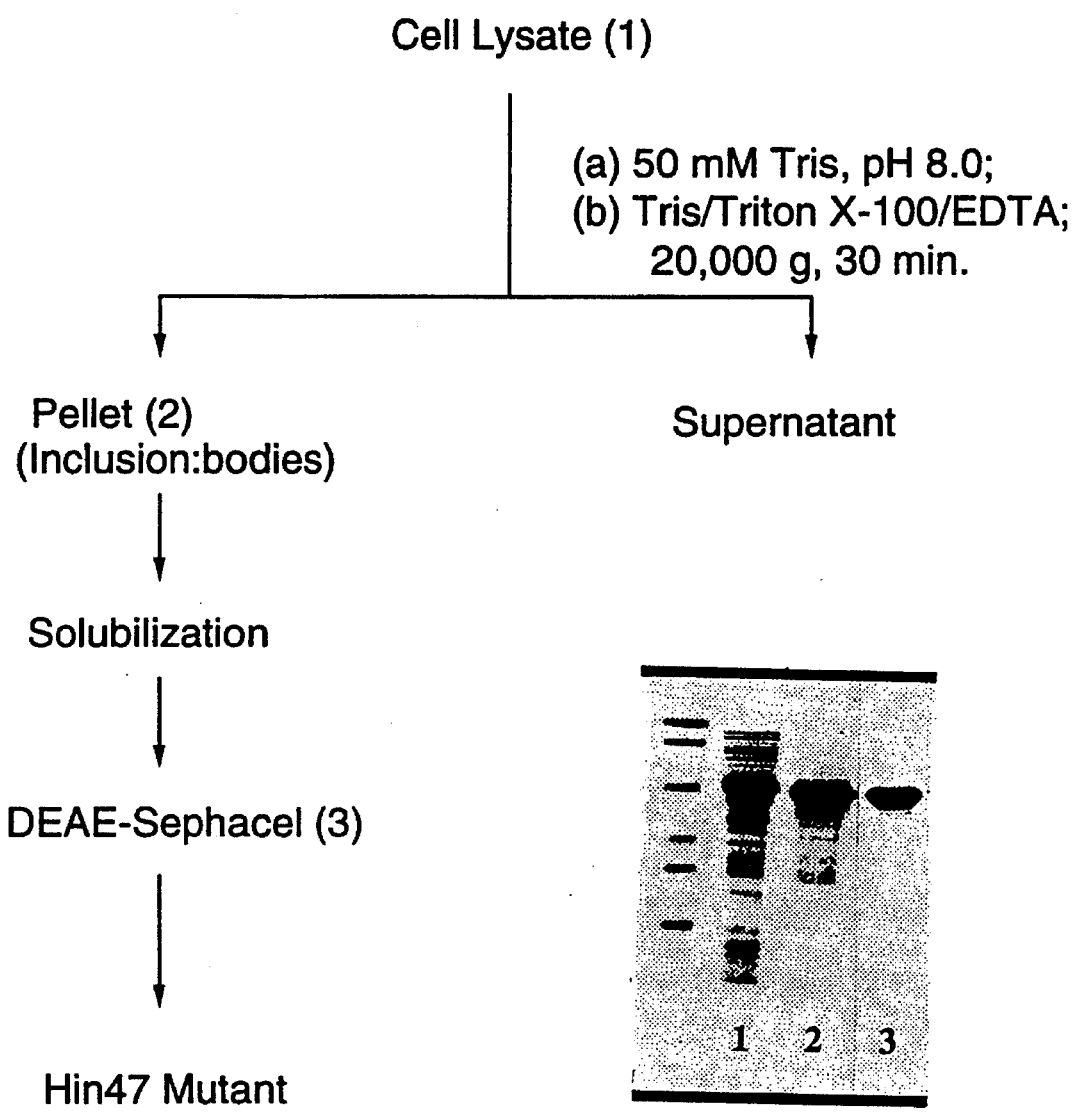
FIG. 6 shows a process for purifying the Hin47 analog from *E. coli* according to one embodiment of the present invention and gel analysis of the purified product.

Referring to FIG. 5, there is illustrated plasmids DS-1011-1-1 and DS-1048-2 which express a Hin47 analog serine-197→alanine in *E. coli*. FIG. 6 shows a flow diagram of a method for the purification of the Hin47 analog from *E. coli* inclusion bodies.

Figure 7:
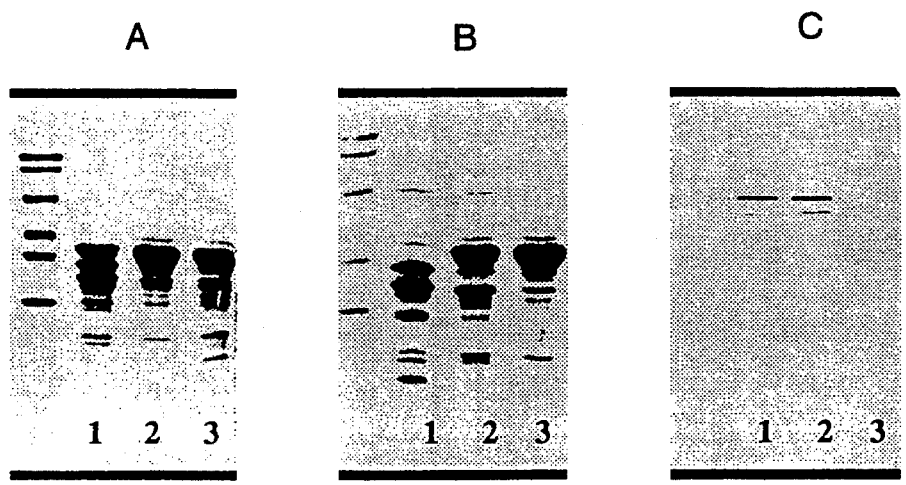
FIG. 7 shows the protease activities of natural Hin47 and Hin47 analog towards β-casein.

FIG. 7 shows the reduced protease activity of the Hin47 serine-197→alanine analog on the substrate β-casein and demonstrates the analog to have less than about 10% of the protease activity of natural Hin47 protein. Thus, in one embodiment of the invention, there is provided an analog of Hin47 having a protease activity of less than about 10% of the protease activity of natural Hin47 and such analog may specifically have amino acid Serine-197 replaced by alanine.

Figure 8:
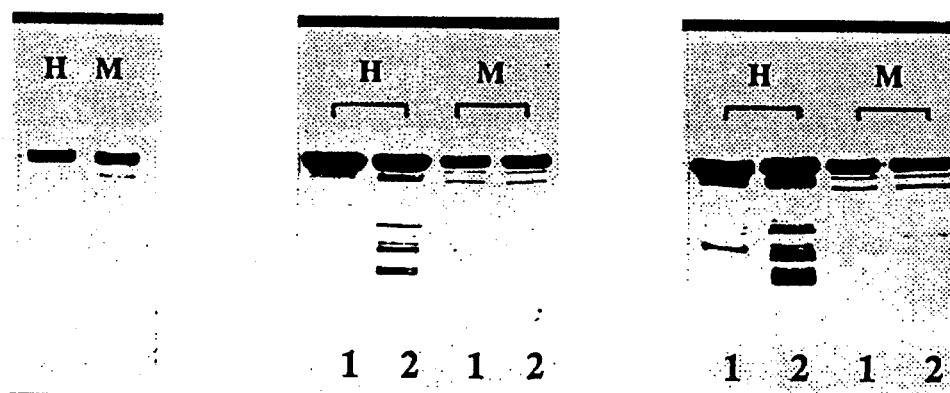
FIG. 8 shows the stability of natural Hin47 and the Hin47 analog at different temperatures.

Referring to FIG. 8, there is illustrated an analysis of the increased stability of an analog of Hin47 as provided herein. Thus, in one embodiment of the present invention, there is provided an analog of Hin47 protein having increased thermal stability, and such analog may specifically have amino acid serine-197 replaced by alanine.

Figure 9:
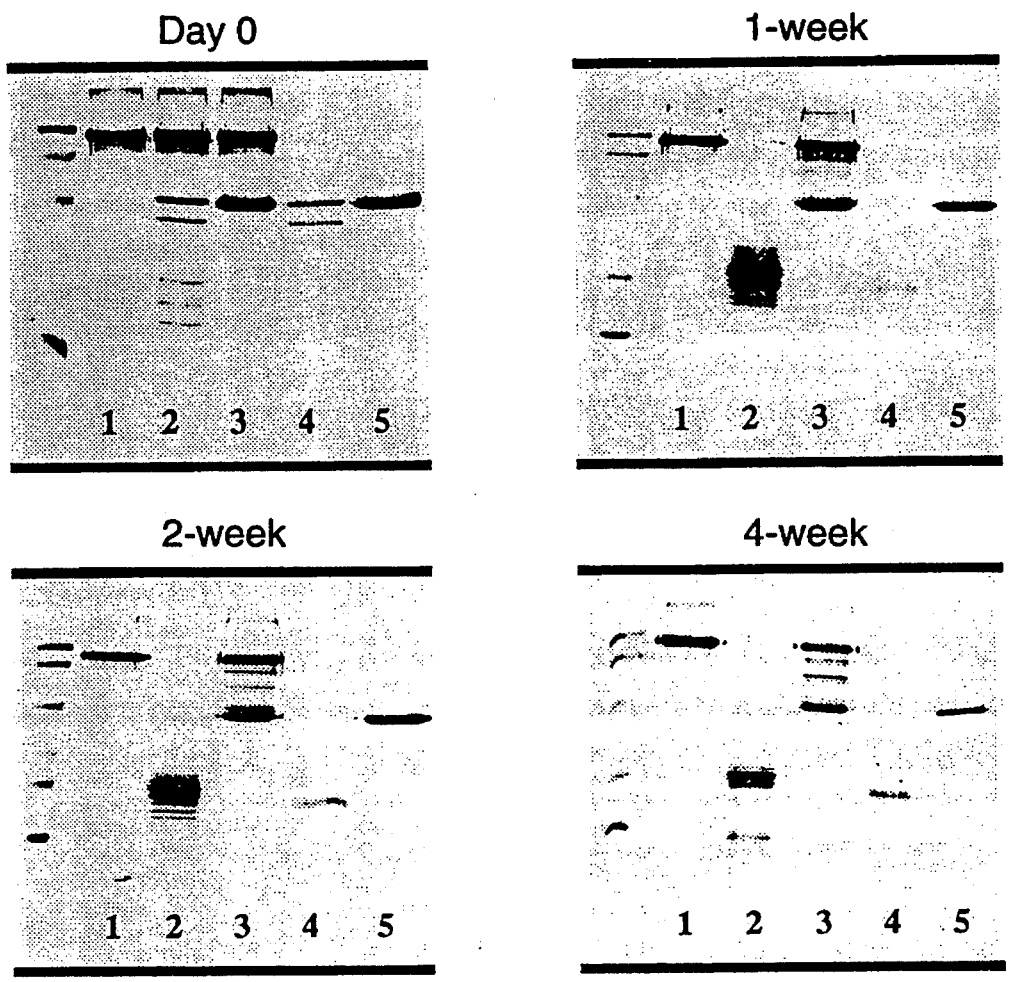
FIG. 9 shows the enzymatic degradation of an *H. influenzae* recombinant protein by natural Hin47 and the Hin47 analog.

Referring to FIG. 9, there is illustrated the proteolytic degradation of a non-Hin47 Haemophilus antigen by Hin47 and a Hin47 analog as provided herein. Thus, in accordance with a further embodiment of the present invention, there is provided an analog of Hin47 compatible with a second non-Hin47 protein and such analog may specifically have amino acid Serine-197 replaced by alanine.

Referring to FIG. 10 and Table 1, there is illustrated the comparative immunogenicity of unmodified Hin47 and a Hin47 analog having reduced protease activity in mice. The Hin47 protein and Hin47 analog had comparable immunogenicity. Thus, in a particular embodiment, there is provided an analog of Hin47 having reduced protease activity and having substantially the same immunogenic properties of natural Hin47 protein. Such analog may specifically have amino acid Serine-197 replaced by alanine.

Referring to Table 2, there is shown the immunoprotective properties of an analog of Hin47 having reduced protease activity against Hib in the infant rat model of bacteraemia, according to an embodiment of the invention and such analog may specifically have amino acid Serine-197 replaced by alanine.

In accordance with another aspect of the present invention, there is provided a vaccine against Haemophilus or other bacterial pathogens that produce Hin47 or a protein capable of inducing antibodies that specifically recognize Hin47, comprising an immunogenically-effective amount of an immunoprotective analog of Hin47 as provided herein or a nucleic acid molecule having a sequence encoding a Hin47 analog as provided herein, and a physiologically-acceptable carrier therefor. The provided analogs also may be used as a carrier protein for hapten, polysaccharides or peptides to make a conjugate vaccine against antigenic determinants unrelated to Hin47.

As will be apparent from the following disclosure, the present invention further provides plasmids and novel strains of bacteria for production of Hin47 analogs as provided herein.

The purified and isolated DNA molecules comprising at least a portion coding for an analog of *Haemophilus influenzae* Hin47 protein having reduced protease activity compared to natural Hin47 typified by the embodiments described herein, are advantageous as nucleic acid probes for the specific identification of Haemophilus strains in vitro or in vivo. The Hin47 analogs encoded by the DNA molecules provided herein are useful as diagnostic reagents as antigens or for the generation of anti-Hin47 antibodies, antigens for the vaccination against the diseases caused by species of Haemophilus and other bacterial pathogens that produce a protein capable of producing antibodies that specifically recognise Hin47 and for detecting infection by Haemophilus and other such bacteria.

In additional embodiments of the present invention, the Hin47 analogs having reduced protease activity as provided herein may be used as carrier molecules to prepare chimeric molecules and conjugate vaccines (including glycoconjugates) against pathogenic bacteria, including encapsulated bacteria. Thus, for example, glycoconjugates of the present inventions may be applied to vaccinations to confer protection against disease and infection caused by any bacteria having polysaccharide antigens including lipooligosaccharides (LOS) and PRP. Bacterial pathogens may include, for example, *Haemophilus influenzae, Streptococcus pneumoniae, Escherichia coli, Neisseria meningitidis, Salmonella typhi, Streptococcus mutans, Cryptococcus neoformans*, Klebsiella, *Staphylococcus aureus* and *Pseudomonas aeruginosa*. Particular antigens which can be conjugated to analogs of Hin47 and methods to achieve such conjugations are described in applicants published PCT application WO 94/12641 which is hereby incorporated by reference thereto.

In another embodiment, the carrier function of Hin47 analogs may be used, for example, to induce immunity toward abnormal polysaccharides of tumor cells, or to produce anti-tumor antibodies that can be conjugated to chemotherapeutic or biocative agents.

Accordingly, the present invention provides the primary sequence and the preparation of an analog of Hin47 of *H. influenzae* that can be used in the prevention and diagnosis of diseases caused by Haemophilus. In particular, the inventors discovered that the Hin47 analog can elicit protective immune response against live *H. influenzae* type b bacterial challenge. Thus, the present inventions have utility in vaccines. The invention also discloses the nucleotide sequences of the gene encoding the Hin47 analog. These DNA segments may be used to provide an immunogen essentially free from other *H. influenzae* antigens, such as PRP and lipooligosaccharides (LOS), through the application of recombinant DNA technology. The Hin47 analog protein, may be produced in a suitable expression system, such as *E. coli*, Haemophilus, Bacillus, Bordetella Fungi, Yeast Baculovirus, Poxvirus, vaccinia or mammalian expression systems. The present disclosure further provides novel techniques which can be employed for preparing essentially pure Hin47 analogs.

It is clearly apparent to one skilled in the art, that the various embodiments of the present invention have many applications in the fields of vaccination, diagnosis, treatment of, for example, Haemophilus infections, and infections with other bacterial pathogens that produce proteins capable of producing antibodies that specifically recognize Hin47 and the generation of immunological reagents. A further non-limiting discussion of such uses is further presented below.

1. Vaccine Preparation and Use

Immunogenic compositions, suitable to be used as vaccines, may be prepared from Hin47 analogs as disclosed herein. The vaccine elicits an immune response in a subject which produces antibodies, including anti-Hin47 antibodies and antibodies that are opsonizing or bactericidal. Should the vaccinated subject be challenged by Haemophilus or other bacteria that produce proteins capable of producing antibodies that specifically recognize Hin47, the antibodies bind to and inactivate the bacterium. Furthermore, opsonizing or bactericidal anti-Hin47 antibodies may also provide protection by alternative mechanisms.

Immunogenic compositions including vaccines may be prepared as injectables, as liquid solutions or emulsions. The Hin47 analogs may be mixed with pharmaceutically acceptable excipients which are compatible with the Hin47 analog. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Methods of achieving adjuvant effect include the use of agents such as aluminum hydroxide or phosphate (alum), commonly used as 0.05 to 0.1 percent solution in phosphate buffered saline. Immunogenic compositions and vaccines may be administered parenterally, by injection subcutaneously or intromuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the Hin47 analogs. The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the Hin47 analogs. Suitable regimes for initial administration and booster doses are also variable, but may include an initial administration followed by subsequent administrations. The dosage may also depend on the route of administration and will vary according to the size of the host.

The concentration of antigen in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

The nucleic acid molecules encoding the Hin47 analog of the present invention may also be used directly for immunization by administration of the DNA directly, for example, by injection for genetic immunization or by constructing a live vector, such as Salmonella, BCG, adenovirus, poxvirus, vaccinia or poliovirus. A discussion of some live vectors that have been used to carry heterologous antigens to the immune system are discussed in, for example, O'Hagen (1992). Processes for the direct injection of DNA into test subjects for genetic immunization are described in, for example, Ulmer et al., 1993.

2. Immunoassays

The Hin47 analogs of the present invention are useful as immunogens for the generation of anti-Hin47 antibodies, as antigens in immunoassays including enzyme-linked immunosorbent assays (ELISA), RIAs and other non-enzyme linked antibody binding assays or procedures known in the art for the detection of anti-bacterial, Haemophilus, and anti-Hin47 antibodies. In ELISA assays, the Hin47 analogs, are immobilized onto a selected surface, for example, a surface capable of binding proteins such as the wells of a polystyrene microtiter plate. After washing to remove incompletely adsorbed Hin47 analogs, a nonspecific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conductive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures such as of the order of about 25° to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound Hin47 analogs, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a color development upon incubating with an appropriate chromogenic substrate. Quantification may then be achieved by measuring the degree of colour generation using, for example, a visible spectra spectrophotometer.

3. Use of Sequences as Hybridization Probes

The nucleic aid molecules of the present invention, having the sequence of the hin47 analog gene, allow for the identification and cloning of the Hin47 genes from any species of Haemophilus and other bacteria that produce proteins capable of producing antibodies that specifically recognize Hin47.

The nucleic acid molecules having the sequence encoding the Hin47 analog of the present invention are useful for their ability to selectively form duplex molecules with complementary stretches of other hin47 genes. Depending on the application, a variety of hybridization conditions may be employed to achieve varying degrees of selectivity of the probe toward the other hin47 genes. For a high degree of selectivity, relatively stringent conditions are used to form the duplexes, such as low salt and/or high temperature conditions, such as provided by 0.02M to 0.15M NaCl at temperatures of between about 50° to 70° C. For some applications, less stringent hybridization conditions are required, such as 0.15M to 0.9M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results.

in a clinical diagnostic embodiment, the nucleic acid molecules encoding the hin47 genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag, such as urease, alkaline phosphatase or peroxidase, instead of a radioactive tag may be used. In the case of enzyme tags, colorimetric indicator substrates are known which can be employed to provide a means visible to the human eye or spectrophotometrically, to identify specific hybridization with samples containing hin47 gene sequences.

The nucleic acid molecules comprising hin47 genes of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the hin47 genes of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label.

4. Expression of the Genes encoding analogs of Hin47 having reduced protease activity Vectors perhaps containing replicon and control sequences which are derived from species compatible with the host cell may be used for the expression of the Hin47 analog genes as provided herein in expression systems. The vector ordinarily carries a replication site, as well as marking sequences which are capable of providing phenotypic selection in transformed cells. For example, E. coli may be transformed using pBR322 which contains genes for ampicillin and tetracycline resistance and thus provides easy means for identifying transformed cells. The pBR322 plasmid, or other microbial plasmid or phage must also contain, or be modified to contain, promoters which can be used by the host cell for expression of its own proteins.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as E. coli LE392.

Promoters commonly used in recombinant DNA construction include the β-lactamase (penicillinase) and lactose promoter systems (Chang et al., 1979; Goeddel et al., 1980) and other microbial promoters, such as the T7 promoter system (U.S. Pat. No. 4,952,496). Details concerning the nucleotide sequences of promoters are known, enabling a skilled worker to ligate them functionally with plasmid vectors. The particular promoter used will generally be a matter of choice depending upon the desired results. Hosts that are appropriate for expression of the Hin47 analogs include E. coli, Bacillus species, Haemophilus Bordetella fungi, yeast, mammalian cells or the baculovirus expression system may be used.

Thus, in accordance with the invention, it may be preferred to make the Hin47 analog protein by recombinant methods. Particularly desirable hosts for expression in this regard include Gram positive bacteria which do not have LPS and are therefore endotoxin free. Such hosts include species of Bacillus and may be particularly useful for the production of non-pyrogenic Hin47 analog.

Biological Deposits

Plasmid DS-1011-1-1 pT7/Hin47* that contains a portion coding for a Hin47 analog that is described and referred to herein has been deposited with the American Type Culture Collection (ATCC) located at Rockville, Maryland, USA, pursuant to the Budapest Treaty on Jul. 27, 1994 under ATCC American No. 75845. Samples of the deposited plasmid will become available to the public upon grant of a patent based upon this United States patent application. The invention described and claimed herein is not to be limited in scope by plasmid deposited, since the deposited embodiment is intended only as an illustration of the invention. Any equivalent or similar plasmids that encode similar or equivalent antigens as described in this application are within the scope of the invention.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example illustrates the cloning of the hin47 gene from non-typable H. influenzae strain SB33.

Chromosomal DNA was prepared from H. influenzae strain SB33, and an EMBL3 library was prepared and screened with a labelled oligonucleotide probe specific for the 5'-end of hin47. Non-typable H. influenzae strain SB33 was grown on Mueller-Hinton agar or in brain heart infusion broth as described by Harkness et al., 1992. Chromosomal DNA was prepared as follows: cells from 50 ml of culture were pelleted by centrifugation at 5000 rpm for 15 to 20 min, at 4° C., in a Sorvall RC-3B centrifuge. The cell pellet was resuspended in 10 ml of TE (10 mM Tris/HCl, 1 mM EDTA, pH 7.5), pronase was added to 500 μg ml$^{-1}$ and SDS to 1%. The sample was incubated at 37° C. until a clear lysate was obtained. The lysate was gently extracted once with Tris-saturated phenol (pH 7.4), once with Tris-saturated phenol/chloroform (1:1) and once with chloroform. The final aqueous phase was dialysed at 4° C. for 24 h against 1M NaCl, followed by 24 h against TE.

An EMBL3 library was prepared by partial digestion of SB33 chromosomal DNA with Sau3A I, followed by size fractionation either on a 10 to 30% sucrose gradient in TNE (20 mM Tris/HCl, 5 mM NaCl, 1 mM EDTA, pH 8.0) or by preparative gel electrophoresis. Fractions containing DNA fragments greater than 5 kb in length were pooled, precipitated and ligated with BamH I arms of EMBL3 (Promega). The ligation mixture was packaged using a Gigapack II packaging kit and plated onto E. coli LE392 cells. The libraries were amplified and stored at 4° C. in the presence of 0.3% chloroform.

Plaques were lifted onto nitrocellulose filters for hybridization with a $^{32}$p-labelled oligonucleotide probe (3026.SL). The oligonucleotide sequence was ATGAAAAAAA-CACGTTTTGTATTAAATAGTATTGCACTTGG (SEQ ID NO: 3) corresponding to the N-terminal amino acid sequence MKKTRFVLNSIALG (SEQ ID NO: 19). Phage DNA was prepared from putative plaques and the insert DNA was excised by Sal I digestion and cloned into pUC8-BgXb digested with Sal I. Plasmids JB-1031-1-14 and JB-1068-2-2 (FIG. 1) were selected for further analysis.

Example 2

This Example illustrates the characterization and sequence analysis of the hin47 gene and deduced amino acid sequence of the Hin47 protein from NTHi strain SB33.

Restriction mapping and Southern blot analysis of clones JB-1031-1-14 and JB-1068-2-2 localized the hin47 gene on a 4.7 kb BamH I/BamH I or a 2.7 kb BamH I/Pst I DNA fragment. The 4.7 kb BamH i/BamH I fragment from JB-1068-2-2 was subcloned into pUC8/BgXb generating plasmid DS-755-1. The 3.1 kb BamH I to Xba I fragment of DS-755-1 was subcloned into pUC18 generating plasmid JB-1165-1 which has restriction sites suitable for the Erase-a-base (Promega) procedure (FIG. 1). This technique generates successive clones with increasing truncations of insert DNA, with the deletions occurring from the same end. The resultant nested set of clones can be sequenced rapidly using a universal primer.

DNA from plasmid JB-1165-1 was digested with BamH I and Sac I and subjected to exoIII digestion using an Erase-a-base kit. The resultant set of truncated plasmids was analysed by agarose gel electrophoresis and representative plasmids were selected for sequence analysis.

Plasmid DNA for sequencing was prepared by a modification of the procedure of Holmes and Quigley, 1981. Briefly, the cell pellet from 50 ml of culture was resuspended in 10 ml STET (8% sucrose, 5% Triton X-100, 50 mM EDTA, and 50 mM Tris/HCl, pH 8.0), lysozyme (2.5 mg) was added and the mixture was boiled for 2 min. The sample was spun at 14,000 rpm in a Sorvall RC 5B for 20 minutes and the supernatant was precipitated with an equal volume of isopropanol, washed with 70% ethanol then absolute ethanol, and then air dried. The pellet was resuspended in 0.9 ml of TE, then 20 µl of 5 mg ml$^{-1}$ RNAse A were added, and the mixture was incubated at 37° C. for 15 min. After the addition of 500 µl of 1.5M NaCl/30% PEG, the mixture was incubated on ice for 30 min and the DNA was pelleted by centrifugation in an Eppendorf microfuge for 10 min. The pellet was resuspended in 400 µl of TE and extracted twice with Tris-saturated phenol (pH 7.4), twice with Tris-saturated phenol/chloroform (1:1) and twice with chloroform. The DNA was precipitated by adding 40 µl of 3M ammonium acetate and 1 ml of ethanol, washed with 70% ethanol and resuspended in distilled water.

DNA samples were sequenced using the ABI model 370A DNA sequencer and the dye terminator chemistry. The universal reverse primer was used with the nested set of clones to determine the sequence of the hin47 coding strand. Oligonucleotide primers of approximately 25 bases in length were used to confirm the sequence of the non-coding strand. The nucleotide sequence of the SB33 hin47 gene and the deduced amino acid sequence of the Hin47 protein are shown in FIG. 2. The nucleotide and N-terminal amino acid sequences of Hin47 presented at the ASM meeting, New Orleans, May 26 to 30, 1992 are indicated in lower case in FIG. 2. The amino terminal sequences of the SB33 Hin47 and this presented sequence are identical, establishing the identity of the cloned gene as hin47.

Example 3

This Example describes the discovery of serine protease activity of Hin47 protein.

The deduced amino acid sequence of Hin47 protein determined in Example 2 above was compared with all other known proteins in the Genbank data base. As described above, Hin47 protein is described in published PCT applications WO 94/00149, WO 92/11367 and WO 92/10936 to be an adhesin molecule of Haemophilus. It was, therefore, a surprising and unexpected discovery of the present invention that Hin47 protein has significant amino acid homolgy (55%) with the serine protease E. coli htrA and S. typhimurium htrA and other proteases. These amino acid sequence homologies are shown in FIGS. 3 and 4. Furthermore, Hin47 protein was found to autodigest unless it was stored in the presence of a serine protease inhibitor, such as Pefablock.

Example 4

This Example illustrates the generation of the mutant hin47 gene by site-directed mutagenesis.

As explained above, H. influenzae Hin 47, E. coli htrA, and S. typhimurium htrA are all serine proteases. The consensus sequence of the active site of serine proteases is GDSGGPK (SEQ ID NO: 18) [Brenner, 1988] with serine being the active residue. The htrA proteins both have a GNSGGAL (SEQ ID NO: 17) sequence and in H. influenzae Hin47, there is the identical sequence between residues 195 and 201 of the mature protein. Thus, the serine residue at position 197 was selected for site-directed mutagenesis, to produce an analog of Hin47 with reduced protease activity.

An oligonucleotide CGCTCCACCAGCATTACCGCGG (SEQ ID NO: 20) was synthesized which would change the serine residue at 197 to an alanine. The hin47 gene was cloned into M13mp18 generating clone DS-981-3 and mutagenesis was performed using the Amersham In Vitro Site-Directed Mutagenesis kit. Clone DS-991-8 was confirmed by sequence analysis to contain the mutation Serine-197 to Alanine. This mutant hin47 gene is designated hin47*.

In addition a comparison of the amino acid sequence of Hin47 with other proteases (as shown in FIG. 4) revealed that amino acids His-91 and Asp-121 are sites appropriate for mutagenesis to produce an analog of Hin47 with reduced protease activity. By mutagenesis methods analogous to those described above, His-91 and/or Asp-121 are deleted or replaced by different amino acids. Such amino acid replacements may include His-91 to Alanine and Asp-121 to Alanine. Olignonucleotides to effect such mutagenesis include:

His-91→Ala-91  5' ATCAATAACAGCATTATTGGT 3' (SEQ ID NO: 21)
Asp-121→Ala-121 5' TAATGCAATTGCTGATAGTTC3' (SEQ ID NO: 22)

Many serine proteases are secreted in an inactive ('zymogen') form, and require clipping to expose their active sites. N terminal sequence analysis of mature natural Hin47 protein suggested the cleavage of the preprotein to occur at KFFG DRFAEQ (SEQ ID NO: 23). Modifications of amino acids that prevent cleavage of the molecule to produce the active protease molecule can produce an analog of Hin47 having reduced protease activity.

Example 5

This Example illustrates the construction of plasmids expressing Hin47 Ser-197→alanine analog from E. coli.

The mutated hin47* gene from plasmid DS-991-8 was cloned into the pT7-7 expression vector to generate plasmid DS-1011-1-1 (FIG. 5). E. coli strain BL21/DE3 was transformed to generate E. coli strain DS-1018-3-1 which expresses Hin47 Ser197→alanine analog upon induction.

In order to utilize tetracycline selection, the hin47* gene was cloned into pBR328. The Bgl II/Cla I T7/hin47* gene fragment from DS-1011-1-1 was cloned into pEVvrf1 (Young and Davis, 1985) in order to generate a Bgl II/BamH I fragment which could be cloned into pUC-4K (Pharmacia) digested with BamH I. The resultant clone DS-1034-3 was digested with EcoR I and the T7/hin47* gene fragment cloned into pBR328 (Boehringer Mannheim Corporation) to generate plasmids DS-1048-2 and DS-1067-2. Electroporation of plasmid DNA into E. coli strain BL21DE3 resulted in strains DS-1071-1-1 and DS-1071-3-1 which express the Hin47 Ser-197→alanine analog.

Example 6

This Example illustrates the expression of Hin47 Ser-197→alanine analog from E. coli.

An overnight culture of strains DS-1018-3-1, DS-1071-1-1, or DS-1071-3-1 were grown overnight in NZCYM media+3% dextrose+antibiotics (ampicillin at 25 µg ml$^{-1}$ or tetracycline at 10 µg ml$^{-1}$), at 37° C., with shaking. A 1:40 dilution of the overnight culture was inoculated into the same medium and grown at 37° C. with shaking until the absorbance was $A_{578}$ approximately 0.3. A 1/10 volume of 10% lactose was then added to induce expression from the T7 promoter. Cell samples were harvested about 4 hours after induction by centrifuging culture samples at 5000 rpm for 10 min in a Sorvall RC-3B, at 4° C.

Example 7

This Example illustrates the extraction and purification of Hin47.

Hin47 was expressed as soluble protein in *E. coli*. The cell pellet from a 250 ml culture, prepared as described in Example 6, was resuspended in 40 ml of 50 mM Tris-HCl, pH 8.0, and disrupted by sonication (3×10 min, 70% duty circle). The extract was centrifuged at 20,000×g and the resulting supernatant which contained >95% of the soluble Hin47 protein was retained. This fraction was called "Hin47-extract".

This Hin47-extract was further purified on a DEAE Sephacel column. Forty ml of the Hin47-extract was applied onto a 20-ml DEAE Sephacel column equilibrated in 50 mM Tris-HCl, pH 8.0. Hin47 bound to the column under these conditions. The column was washed with 100 ml of 50 mM Tris-HCl, pH 8.0, and then washed with 100 ml of 500 mM Tris-HCl, pH 8.0 containing 20 mM NaCl. Hin47 was then eluted with 50 mM Tris-HCl, pH 8.0, containing 40 mM NaCl. The amount of Hin47 in the fractions was determined by the BCA protein assay. The purity of Hin47 was assessed by SDS-PAGE analysis. The fractions containing Hin47 were combined and stored at –20° C.

Example 8

This Example illustrates the extraction and purification of Hin47 Ser-197→alanine analog.

Hin47 Ser-197→alanine analog was expressed in inclusion bodies in *E. coli*. The cell pellet from a 250 ml culture, prepared as described in Example 6, was resuspended in 40 ml of 50 mM Tris-HCl, pH 8.0, and disrupted by sonication (3×10 min, 70% duty circle). The extract was centrifuged at 20,000×g and the resulting pellet was saved. The pellet was re-extracted with 40 ml of 50 mM Tris-HCl, 0.5% Triton X-100, 10 mM EDTA, pH 8.0. The suspension was sonicated 10 min at 70% duty circle. The extract was centrifuged at 300×g for 5 min. The resultant supernatant was centrifuged again at 20,000×g for 30 min and the resultant pellet was saved. The pellet was resuspended in 50 mM Tris-HCl, 0.5% Triton X-100, 10 mM EDTA, pH 8.0. The suspension was then mixed with 50 mM Tris-HCl, pH 8.0 containing 8M urea. The final urea concentration in the mixture was adjusted to 2M with 50 mM Tris-HCl, pH 8.0. Hin47 Ser-197→alanine analog was completely solubilized under there conditions. The final volume of the solution was 20 ml. This fraction is called "Hin47 analog-extract". The Hin47 analog-extract was further purified on a DEAE Sephacel column. Twenty ml of Hin47 analog-extract was applied onto a 10 ml DEAE Sephacel column equilibrated in 50 mM Tris-HCl, pH 8.0. Hin47 Ser-197→alanine analog bound to the column under these conditions. The column was washed with 50 mM Tris-HCl, pH8.0, and Hin47 analog was eluted with 50 mM Tris-HCl, pH 8.0, containing 30 mM NaCl. The amount of Hin47 analog in the fractions was determined by the BCA protein assay. The purity of Hin47 analog was assessed by SDS-PAGE analysis (FIG. 6). The fractions containing Hin47 analog were combined and stored at –20° C.

Example 9

This Example illustrates the protease activity of Hin47 and Hin47 Ser-197→alanine analog.

The enzymatic activity of Hin47 and Hin47 Ser-197→alanine analog was analyzed using β-casein as a substrate (FIG. 7). The reaction mixtures contained 5 μg of β-casein and either Hin47 or Hin47 analog. The reaction was carried out at 37° C. for two hours, and then stopped by adding the SDS-sample buffer and instantly heating the sample at 100° C. for 5 min. The aliquots were anlyzed by SDS-PAGE. As shown in FIG. 7, digestion of β-casein by Hin47 was more obvious after two hours (panel A, lane 1) in comparison to the fractions containing Hin47 analog (panel A, lane 2) or without any exogenous proteins (panel A, lane 3). The presence of Hin47 or Hin47 analog in these mixtures were confirmed by immuno-blotting using a monoclonal antibody to Hin47 (FIG. 7, panel C, lanes 1 and 2).

The protease activities of Hin47 and Hin47 Ser-197→alanine analog were also compared by analyzing the auto-digestion of Hin47 or Hin47 analog at 4° C. and –20° C. The purified Hin47 or analog were stored at either 4° C. or –20° C. for up to 20 days. Aliquots were taken on days 0, 10 and 20 and the stability of Hin47 or analog was analyzed by immuno-blotting using a Hin47 monoclonal antibody (FIG. 8). The analog was much more stable than Hin47 up to 20 days when stored at either 4° C. or –20° C.

To further examine the protease activity of the Hin47 Ser-197→alanine analog, the ability of Hin47 or analog to degrade an 80kDa *H. influenzae* recombinant antigen was examined. Thus, a mixed antigen study was performed to determine the proteolytic effect of Hin47 or Hin47 analog on another antigen. An 80 kDa *H. influenzae* recombinant protein (TBP1) was chosen for this study in order to distinguish it from the Hin47 or analog protein (47 kDa). Five mixtures were formulated as follows: 80-kDa). Five mixtures were formulated as follows: 80-kDa protein alone; 80-kDa protein+Hin47; 80-kDa protein+analog; Hin47 alone; and analog alone. The amount of each protein in the mixture was 5 μg. The mixtures were stored at 4° C. up to four weeks. Aliquots were taken on days 0, 7,14 and 28 for analysis by SDS-PAGE (FIG. 9). Both the 80 kDa protein and Hin47 were largely degraded after one week (lanes 2 and 4). In contrast, the 80 kDa protein in combination with Hin47 analog remained intact after one week, and showed only slight degradation even after four weeks (lane 3).

Example 10

This Example illustrates the comparative immunogenicity of Hin47 and Hin47 analog in mice. The results of a study to determine the comparative immunogenicity of Hin47 and the Hin47 Ser-197→alanine analog are shown in FIG. 10. Thus, groups of five Balb/c mice were injected three times (as indicated by arrows) s.c. on days 1, 29 and 43 with 1-μg dose of either Hin47 or Hin47 analog in the presence of $AlPO_4$ (1.5 mg per dose). Blood samples were taken on days 14, 28, 42 and 56 (as indicated by bleeds 1, 2, 3 and 4, respectively) for analyzing the anti-Hin47 antibody titers by EIAs. The determination of anti-Hin47 antibodies in mouse sera was performed as described by Panezutti et al. (1993). Microtiter wells were coated with 1 μg of either Hin47 or analog for 16 hours at room temperature. The plates were then blocked with 0.1% (w/v) bovine serum albumin in PBS. The mouse sera were serially diluted, added to the wells, then incubated for one hour at room temperature. Affinity-purified F(ab')$_2$ fragments of goat anti-mouse IgG (Fc specific) antibody conjugated to horseradish peroxidase were used as the second antibody. The reactions were developed using tetramethylbenzidine (TMB/ H$_2$O$_2$) and absorbencies were measured at 450 nm (using 540 nm as a reference wavelength) in a Flow Multiskan MCC microplate reader. The reactive titer of an antiserum was defined as the reciprocal of the dilution consistently showing a two-fold increase in absorbance over that obtained with the pre-bleed serum sample. As can be seen from FIG. 10, both Hin47 and the Hin47 analog elicited comparable IgG titers in mice regardless of whether Hin47 or mutant was used as an anitgen in EIAs.

To further examine the immune response to Hin47 or the Hin47 Ser-197→alanine analog, the subclasses of anti-Hin47 IgG in mouse sera were determined. Microtiter wells sere coated with 1 µg of purified Hin47 or analog. The final bleed of mouse serum samples from the comparative immunogenicity study (as described above) were pooled and tested in EIAs. Rat anti-mouse IgG$_1$, IgG$_{2a}$, IgG$_{2b}$ antibodies conjugated horseradish peroxidase and rabbit anti-mouse IgG$_3$ conjugated to horseradish peroxidase were used as reagents in EIAs. The working dilution of each conjugate was determined using purified antibody subclasses to avoid cross reactivity. The reactive titers were determined as described above. As shown in Table 1 below, the IgG-subclass profile induced in mice by either Hin47 or Hin47 analog were identical, regardless of whether Hin47 or analog was used as a solid antigen in the EIAs. The predominant IgG response in both groups of mouse sera was of the IgG$_1$ isotype. Hence, the Hin47 analog exhibited substantially the same immunogenic properties as the natural protein.

Example 11

This example illustrates the immunoprotective properties of Hin47 and Hin47 Ser-197→alanine analog.

The immunoprotective properties of Hin47 and the Hin47 Ser-197→alanine analog were analyzed by the ability of Hin47 specific antisera to protect infant rats against *H. influenzae* type b strain MinnA in a bacteremia model. The results of this study are shown in Table 2 below. Groups of nine 6-day old Wistar infant rats were inoculated subcutaneously (s.c.) on the dorsum close to the neck with 0.1 mL of either a rabbit anti-Hin47 analog antiserum or the corresponding prebleed serum. Twenty-four hours later, the animals were challenged intraperitoneally (i.p.) with 700 cfu of freshly grown Hib strain MinnA. Blood samples were collected 20 hours post-challenge and plated onto chocolate agar plates. Bacterial colonies were counted after 24 hours. As shown in Table 2, three out of nine animals in the group inoculated with anti-Hin47 analog antiserum did not show any bacteremia in their blood. Only one mouse in the group inoculated with anti-Hin47 analog antiserum (11%) had a higher bacteria recovery from the blood sample compared to mice inoculated with prebleed serum. In contrast, bacteria were recovered from all the nine mice inoculated with pre-bleed serum. Four out of nine animals (44%) in the group inoculated with pre-bleed serum showed high levels (500 to 1,000) of bacteria recovered in blood samples.

SUMMARY OF DISCLOSURE

In summary of this disclosure, the present invention provides a novel analog of *Haemophilus influenzae* Hin47 protein which has a decreased protease activity of less than about 10% of that of the natural Hin47 protein as well as isolated and purified DNA molecules encoding the same.

TABLE 1

Hin47 IgG titers in mouse immune sera

| IgG Suclass | IgG titers in Group #1* | | IgG titers in Group #2* | |
|---|---|---|---|---|
| | To Hin47 | To Mutant | To Hin47 | To Mutant |
| IgG(H + L) | 102,400 | 102,400 | 102,400 | 102,400 |
| IgG$_1$ | 25,600 | 25,600 | 25,600 | 25,600 |
| IgG$_{2a}$ | <100 | <100 | <100 | <100 |
| IgG$_{2b}$ | 400 | 400 | 400 | 400 |
| IgG$_3$ | <100 | <100 | <100 | <100 |

*Group #1: Immune sera were pooled from a group of five mice received Hin47 immunization.
Group #2: Immune sera were pooled from a group of five mice received Hin47 mutant immunization.
Plates were coated with either Hin47 or mutant protein.

TABLE 2

Protective ability of rabbit Anti-Hin47 Mutant antiserum against Hib in infant rat model of bacteremia

| | Number of Animals cfu of Bacteria/2.5 µL Blood | | | | |
|---|---|---|---|---|---|
| Antibody | Av.0 | Av.50 (10–100) | Av.200 (100–300) | Av.650 (300–1,000) | Total Animals |
| Anti-Hin47* | 3 | 3 | 2 | 1 | 9 |
| Prebleed | 0 | 4 | 1 | 4 | 9 |

Groups of nine 6-day old infant rats were immunized s.c. with either a rabbit anti-Hin47 mutant antiserum or the corresponding prebleed serum. Animals were challenged i.p. with 700 cfu *H. influenzae* strain MinnA after 24 hours. The blood samples were taken at 20 hours after the challenge.

Anti-47* antibody: rabbit immune serum raised against purified Hin47 mutant in CFA/IFA.

Average bacteria recovery from immunized group: 100 cfu per 2.5 µL of blood; from control group: 290 cfu per 2.5 µL of blood.

Reference List

1. Zangwill et al, 1993 MMWR 42:1–15.
2. Schoendorf et al, 1994 Pediatrics 93:663–8.
3. Brenner et al, 1988 Nature 334:528–530.
4. O'Hagan 1992 Clin. Pharmokinet. 22:1–10.
5. Ulmer et al, 1993 Curr. Opinion. Invest. Drugs 2:983–989.
6. Chang et al, 1978 Nature 275:617.
7. Goeddel et al 1980 Nucl. Acid. Res. 8:4057.
8. Harkness et al, 1992 J. Bacteriol. 174:2425–2430.
9. Loeb et al, 1987 Infec. immun. 55:2612–2618.
10. Holmes and Quigley 1981. Analyt. Biochem. 114:193–197.
11. Young and Davis 1985 Gene 38:31–38.
12. Panezutti et al, 1993 Infec. Immun. 61:1867–72.

What we claim is:

1. An isolated and purified analog of *Haemophilus influenzae* Hin47 protein having a decreased protease activity which is less than about 10% of that of natural Hin47 protein, wherein at least one amino acid of the natural Hin47 protein contributing to protease activity and which is selected from the group consisting of amino acids 91, 121 and 195 to 201 of natural Hin47 protein has been deleted or replaced by a different amino acid to provide said reduced protease activity.

2. The analog of claim 1 having substantially the same immunogenic properties as natural Hin47 protein.

3. The analog of claim 1 wherein said at least one amino acid is Serine-197.

4. The analog of claim 3 wherein Serine-197 is replaced by alanine.

5. The analog of claim 1 wherein Histidine-91 is replaced by alanine, lysine or arginine.

6. The analog of claim 1 wherein Asp-121 is replaced by alanine.

7. An isolated and purified nucleic acid molecule comprising a mutant *Haemophilus influenzae* hin47 gene coding an analog of *Haemophilus influenzae* Hin47 protein having a decreased protease activity which is less than about 10% of that of natural Hin47 protein, wherein at least one codon of a wild-type hin47 gene encoding an amino acid contributing to protease activity which is the codon encoding an amino acid selected from the group consisting of amino acids 91, 121 and 195 to 201, has been deleted or replaced by a codon encoding a different amino acid to provide the reduced protease activity.

8. The nucleic acid molecule of claim 7 wherein said encoded analog has substantially the immunogenic properties of natural Hin47 protein.

9. The nucleic acid molecule of claim 7 wherein the at least one codon is that encoding Serine-197.

10. The nucleic acid molecule of claim 9 wherein the codon encoding Serine-197 is replaced by a codon encoding alanine.

11. The nucleic acid molecule of claim 7 wherein the codon encoding His-91 is replaced by a codon encoding alanine, lysine or arginine.

12. The nucleic acid molecule of claim 7 wherein the codon encoding Asp-121 is replaced by a codon encoding alanine or glutamic acid.

13. The nucleic acid molecule of claim 7 wherein said mutant gene is formed by site-directed mutagenesis of a wild-type hin47 gene.

14. A recombinant plasmid adapted for transformation of a host cell comprising a plasmid vector into which has been inserted the nucleic acid molecule of claim 7..

15. The recombinant plasmid of claim 14 which is plasmid DS-1011-1-1 (pT7/Hin47*) deposited under ATCC designation 75,845.

16. A transformed cell containing the recombinant plasmid of claim 14.

17. A method for producing an analog of *Haemophilus influenzae* Hin47 protein having a reduced protease activity which is less than about 10% of natural Hin47 protein, which comprises:

identifying at least one amino acid residue of Hin47 protein which contributes to protease activity thereof;

effecting site-directed mutagenesis of the hin47 gene to remove or replace a nucleotide sequence encoding at least one amino acid selected from the group consisting of amino acids 91, 121 and 195 to 201 of the natural Hin47 protein and to produce a mutated hin47 gene;

introducing the mutated hin47 gene into a cell to produce a transformed cell; and growing the transformed cell to produce the Hin47 analog.

18. The method of claim 17 wherein said at least one amino acid is Serine-197.

19. The method of claim 18 wherein Serine-197 is replaced by alanine.

20. The method of claim 17 wherein Histidine-91 is replaced by alanine, lysine or arginine.

21. The method of claim 17 wherein Asp-121 is replaced by alanine or glutamic acid.

22. The method of claim 17 wherein said introduction of the mutated hin47 gene produces a transformed cell in which the mutated hin47 gene is under control of the T7 promoter, and said growing of said transformed cell and expression of the Hin47 analog by said T7 promoter is effected by culturing in an inducing concentration of lactose.

23. The method of claim 22 wherein said introduction of the mutated hin47 gene is effected by transforming said cell with the recombinant plasmid DS-1011-1-1 (pT7/Hin47*) deposited under ATCC designation 75,845.

24. A method of providing an isolated and purified analog of *Haemophilus influenzae* Hin47 protein having a reduced protease activity which is less than about 10% of natural Hin47 protein, which comprises:

identifying at least one amino acid residue of Hin47 protein which contributes to protease activity thereof;

effecting site-directed mutagenesis of the hin47 gene to remove or replace a nucleotide sequence encoding at least one amino acid selected from the group consisting of amino acids 91, 121 and 195 to 201 of the natural Hin47 protein and to produce a mutated hin47 gene;

introducing the mutated hin47 gene into a cell to produce a transformed cell;

growing the transformed cell to produce grown transformed cells harbouring inclusion bodies containing the Hin47 analog;

disrupting said grown transformed cells to produce supernatant and said inclusion bodies;

solubilizing said inclusion bodies to produce a solution containing Hin47 analog;

chromatographically purifying said Hin47 analog from said solution free from cell debris; and isolating said purified Hin47 analog.

25. The method of claim 24 wherein said introduction of the mutated hin47 gene is under control of the T7 promoter, and the growing of said transformed cell and expression of the Hin47 analog by said T7 promoter is effected by culturing in an inducing concentration of lactose.

26. A chimeric molecule, comprising an analog as claimed in claim 1 linked to a polypeptide, protein or a polysaccharide.

* * * * *

UNITED STATES PATENT AND TRADEMARK OFFICE
CERTIFICATE OF CORRECTION

PATENT NO.    : 5,506,139
DATED         : April 9, 1996
INVENTOR(S)   : Loosmore et al It is certified that error appears in the above-identified patent and that said Letters Patent is hereby corrected as shown below:

Drawings,
In figure 4B, under #(Asp102), on line SGBE: "PNNDYGIVRYTNTTIPX" should read -- PNNDYGIVRYTNTTIPK --. Please see attached drawings.

Signed and Sealed this

Fourteenth Day of May, 2002

*Attest:*

*Attesting Officer*

JAMES E. ROGAN
*Director of the United States Patent and Trademark Office*

FIG. 4B.

```
SGBE   : TYYFLTAGHCT------D-------GATT--WA------------NS-ARTVL
SGA    : VAHALTAGHCT------------NISASW-----------------SI
ALP    : TKGFVTAGHCGIVN-------AT-AR-IG-----------GAVVG
Sal.T: KGYVVTNNHVVDNASVIKVQLSDGR
hin47  : KGYVLTNNHVVDEA              DK-IT-VQ-------------LQDGRE
con    : <----|----X----|---->                    <----|---X---|--->
         ********

# (Asp102)
TCN    : RQS-FRHPDYIPLI¦PVHD¦--SNDIMLHLSEPADITGGVKV------
PKAAB  : TAD-FTHRGFNLSAD-GKDY--SHDIMLRLQSPAKTIDAVKV-------
PTN    : SKS-IVHPSYN------SNTL--NNDIMLIKLKSAASLNSRVAS----
CHAA   : AKV-FRNSKYN------SLTI--NNDITLIKLSTAASFSQTVSA----
EST    : QKI-VVHPYWN------TDDVAAGYDIALRLAQSVTLNSVVQL-----
RP2A   : EKQ-TIHESYN------SVEN--LHDIMLLKLEKKVELTPAVN-----
SGT    : TKV-LQARGYN------G-T---GKWALIKLAQPIN--------QPT-
SGBE   : GTT-SGS-SF------------PANDYGIVRYINITIPK--------DGIVG------
SGA    : GIR-TGT-SF------------PNDYGITRHSNPAAA--------DGRVYLMGS---
ALP    : -TFAARV--F------------PGNDRAWSLTSAQTL--------LPRVANGSS
hin47  : FKAKLVG          KDEL SDIALVQLERPSNL TEIKFADSIKLRVGDF
con    : X----|----X                ****    ****    <----|---
                                                   *********
```